United States Patent
Shibusawa et al.

(10) Patent No.: US 6,608,672 B1
(45) Date of Patent: Aug. 19, 2003

(54) SOIL SURVEY DEVICE AND SYSTEM FOR PRECISION AGRICULTURE

(75) Inventors: Sakae Shibusawa, Tokyo (JP); Atushi Ohtomo, Kumamoto (JP); Shinichi Hirako, Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 09/700,305
(22) PCT Filed: Nov. 10, 1999
(86) PCT No.: PCT/JP99/06264
§ 371 (c)(1), (2), (4) Date: Apr. 12, 2001
(87) PCT Pub. No.: WO00/54566
PCT Pub. Date: Sep. 21, 2000

(30) Foreign Application Priority Data

Mar. 15, 1999 (JP) .............................................. 11-69038

(51) Int. Cl.⁷ .............................................. G01N 21/00
(52) U.S. Cl. ...................... 356/73; 356/445; 250/341.2; 250/339.11
(58) Field of Search .......................... 356/73, 445, 417, 356/418; 250/341.2, 339.11, 339.12, 341.8

(56) References Cited

U.S. PATENT DOCUMENTS 5,044,756 A * 9/1991 Gaultney et al. ............. 356/72

* cited by examiner

Primary Examiner—Cassandra Spyrou
Assistant Examiner—Fayez Assaf
(74) Attorney, Agent, or Firm—Crowell & Moring LLP

(57) ABSTRACT

An optical soil survey device to survey the optical characteristics of a given underground soil, a soil survey device to survey the soil, a soil survey system and a mobile soil survey vehicle to survey the soil are disclosed. The disclosed devices and systems may be used to survey the characteristics of a given soil for agricultural purposes. This survey can be carried out without experiencing significant resistance from the soil. A plow-shaped optical soil survey device may be provided with a plow-shaped main unit, whose forward extremity turns up soil; a frame, which supports the sensor and connects a tractor and a main unit; a spectrometer, which is mounted on the frame; a wheel, which surveys the depth of the furrow and is connected to the main unit via an arm; and a survey control unit, which is mounted on the tractor.

29 Claims, 21 Drawing Sheets

X axis

Slit beamed image after image processing

X axis

Total number of pixels

X axis

SOIL SURVEY DEVICE AND SYSTEM FOR PRECISION AGRICULTURE

FIELD OF THE INVENTION

This invention concerns an optical soil survey device to survey the optical characteristics of a given soil, a soil survey device to survey the soil, a soil survey system and a mobile soil survey vehicle to survey the soil. More specifically, it concerns the devices mentioned above which create, at a desired depth, a space in order to survey the characteristics of the soil.

This invention is used for precision agriculture, or farming for precision field management which is a relatively new agricultural concept.

PRIOR ART

In recent years the concept of precision field management has become increasingly popular as a means of preserving the environment and at the same time insuring a profit. The objective is to reduce the amount of investment required to purchase agricultural materials, fertilizer, feed, and so on. The most crucial requirement for precision field management is an accurate understanding of the soil conditions which prevail in a given field. Soil, after all, is the most important element in agricultural production.

When light is projected onto the soil, it is absorbed. It is well known that the wavelength and intensity of the absorbed light will vary with the components of the soil and their quantities. Accordingly, the reflected wave will display characteristic optical spectra (i.e., absorbed spectra) depending on the components of the soil.

Heretofore, then, it was found to be possible to analyze the composition of soil by surveying and analyzing its optical spectra.

An example of an optical soil survey device to survey the optical characteristics of a soil in order to investigate soil conditions in a given field is disclosed in U.S. Pat. No. 5,044,756, which is pictured in FIGS. 19 through 21.

FIG. 19 is a cross section of the part of the device which, while mounted on a vehicle, moves the survey surface of the earth to excavate and examine the soil. Excavation and sensing unit 20 is composed of casing 21, which, as the vehicle advances, progressively excavates the soil. Cutting end 23, which turns up soil 22 as the vehicle advances in direction A, is on the front end of unit 20. The lower portion of the soil near the survey surface which is turned up by cutting end 23 is compressed by casing 21 to produce a flat soil survey surface 24.

Inside casing 20, in the portion facing soil survey surface 24, is an opening 26 which creates a chamber 25. In this chamber the characteristics of the soil are surveyed. On the ceiling of chamber 25 are red light-emitting diodes 28, which project light onto soil survey surface 24, and photodiodes 29, which receive the light reflected off the soil. A cable 27 is used for wiring.

With this design, cutting end 23 on the front of casing 21 turns up soil 22 and creates flat survey surface 24, and as this is happening the characteristics of the soil are surveyed at survey surface 24.

As casing 20 advances, some of the soil which constitutes survey surface 24 moves into chamber 25, which eventually fills up with soil. When this happens, it becomes impossible to survey the characteristics of the soil on survey surface 24.

To address this problem, the device disclosed in U.S. Pat. No. 5,044,756 has an opening 32 in the back of chamber 24 through which the soil which has entered the chamber can escape.

Because casing 21 is advancing quite close to the survey surface of the ground, stray light from the survey surface is apt to enter the chamber through this opening. Thus the escape hole for the soil is made as small as possible.

FIG. 20 is a view of the device in FIG. 19 from underneath. The tip 23a of cutting end 23 is formed at an acute angle so that it can easily cut through the soil.

FIG. 21 is a perspective drawing of the device in operation.

As is discussed above, the aforesaid device to survey optical soil characteristics which is disclosed in U.S. Pat. No. 5,044,756 has a cutting end 23 on the front of its casing 21. As this cutting end 23 turns up soil 22 and creates a flat survey surface 24, it treats this survey surface as the object of investigation in order to survey the characteristics of the soil.

The prior art device to survey the optical characteristics of the soil which is described above has the following shortcomings.

(1) As can be seen in FIG. 20, the tip 23a of cutting end 23 on the front of casing 21 is formed as an acute angle so that it can easily turn up soil 22. As is shown in FIG. 19, as cutting end 23 proceeds it turns up a depth of soil which extends from ground level 30 to soil survey surface 24, that is, the depth indicated by H in FIG. 19. And as can also be seen in FIG. 20, the width T of casing 21 is considerable. As a result, cutting end 23 encounters significant resistance from the surrounding soil as it proceeds, removing the soil and digging a furrow of width T and depth H.

(2) Because casing 21 moves along quite close to the survey surface of the ground, stray light is apt to enter sensing chamber 25. To prevent the entry of stray light, opening 32 to evacuate soil from the chamber is kept very small; however, the small size of opening 32 makes it liable to become clogged with particles of the surrounding soil. When this happens, dirt begins to accumulate in chamber 25 and it becomes impossible to survey the characteristics of the soil.

The object of this invention is to provide an optical soil survey device to survey the optical characteristics of a given soil, a soil survey device to survey the soil, a soil survey system and a mobile soil survey vehicle to survey the soil, all of which, survey the optical characteristics of a given soil which would, without experiencing significant resistance from the soil, be able to survey the various components of the soil and/or the optical characteristics of the soil accurately and without being affected by stray light.

SUMMARY OF THE INVENTION

To survey the characteristics of a soil (including both optical, electrical characteristics, and other types of characteristics detected by other types of sensors), it is necessary to ascertain the depth of the soil being treated. Thus to survey soil characteristics at a given depth, we must excavate the soil in such a way as to form a survey surface at that depth which we can examine. The space required to operate the sensor which examines the soil must be kept to a minimum, and it should be as close as possible to the aforesaid survey surface. If this is done, not much of the soil above the survey space need be excavated, so less resistance is offered by the soil when it is excavated. The shaft extending upward from the survey surface to the ground which accompanies excavation is kept small, which minimizes the pernicious effect of stray light on an optical survey of the soil characteristics which is experienced when sunlight penetrates the aforesaid survey chamber via this shaft.

However, if a construction tool to create such a subterranean chamber is to be driven with a vehicle which traverses the survey surface, the two will somehow have to be conjoined. It is thus impossible to avoid creating some degree of furrow on the survey surface of the ground. To reduce the quantity of stray light which strikes the sensor, we must refill this furrow with soil so that it does not furnish a route for stray light. The basic concept underlying this invention, then, is to realize a design such that very little of the soil above the survey chamber is turned up, or if it is turned up and a furrow is left, such that the furrow is immediately refilled so as to minimize the pernicious effect of stray light.

DETAILED DESCRIPTION OF THE PREFERRED EMBODIMENTS

In this section we shall provide a detailed explanation, with reference to the appended drawings, of preferred embodiments of a soil survey system in which the optical soil survey device to survey the optical characteristics of the soil, the soil survey device to survey the soil, the soil survey system and the mobile soil survey vehicle are implemented according to this invention.

Figure 1:
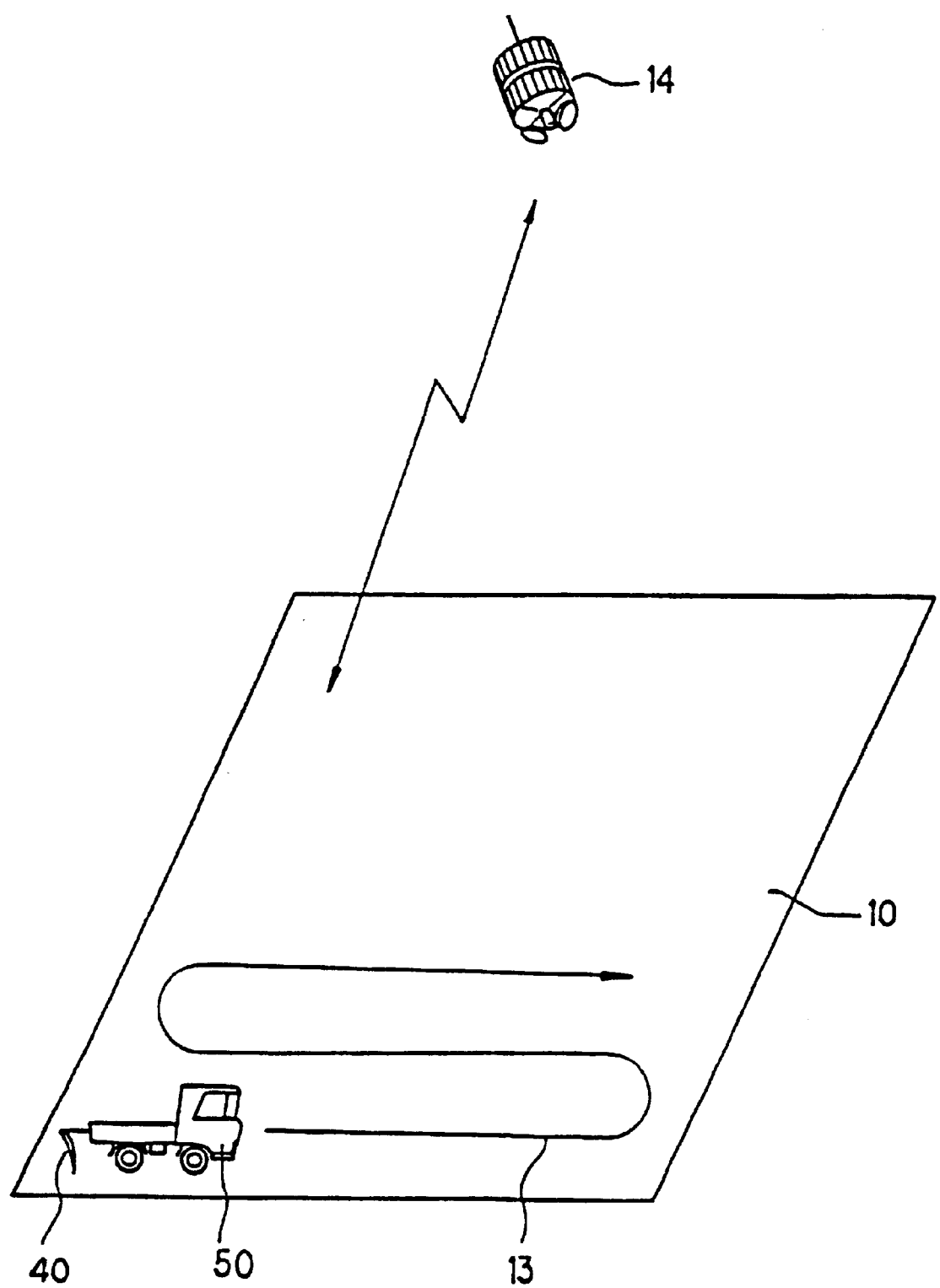
FIG. 1 is a rough sketch of an embodiment of a soil survey system in which an optical soil survey device to survey the optical characteristics of the soil, a soil survey device, a soil survey system and a mobile soil survey vehicle according to this invention have been implemented.

FIG. 1 is a simple sketch showing how soil characteristics are surveyed using a mobile soil survey vehicle in which this invention has been implemented. The device surveys the soil characteristics in the various parts of field 10.

The sensor which surveys the characteristics of the soil is mounted to tractor 50 in FIG. 1 so that it can be mobile. Various types of sensors are available. Some survey the soil's electrical characteristics, while others survey its reflection and absorption characteristics with respect to microwave radiation or detect its chemical properties. Here we shall explain a method to survey the characteristics of the soil in which a device to survey optical characteristics is mounted on tractor 50.

To survey the characteristics of the soil in field 10, plow-shaped optical soil survey device 40 is mounted on the rear of tractor 50 so that it can move forward through the earth. Traversing field 10 in zig-zag fashion as indicated by arrow 13, device 40 researches the characteristics of the soil in every portion of the field.

The current position of tractor 50 in field 10 is obtained by means of a signal transmitted from DGPS (Differential Global Positioning System) satellite 14. The condition of the soil in the various parts of field 10 is discovered using the survey results obtained by optical soil survey device 40 and the current position data obtained from DGPS satellite 14.

Figure 2:
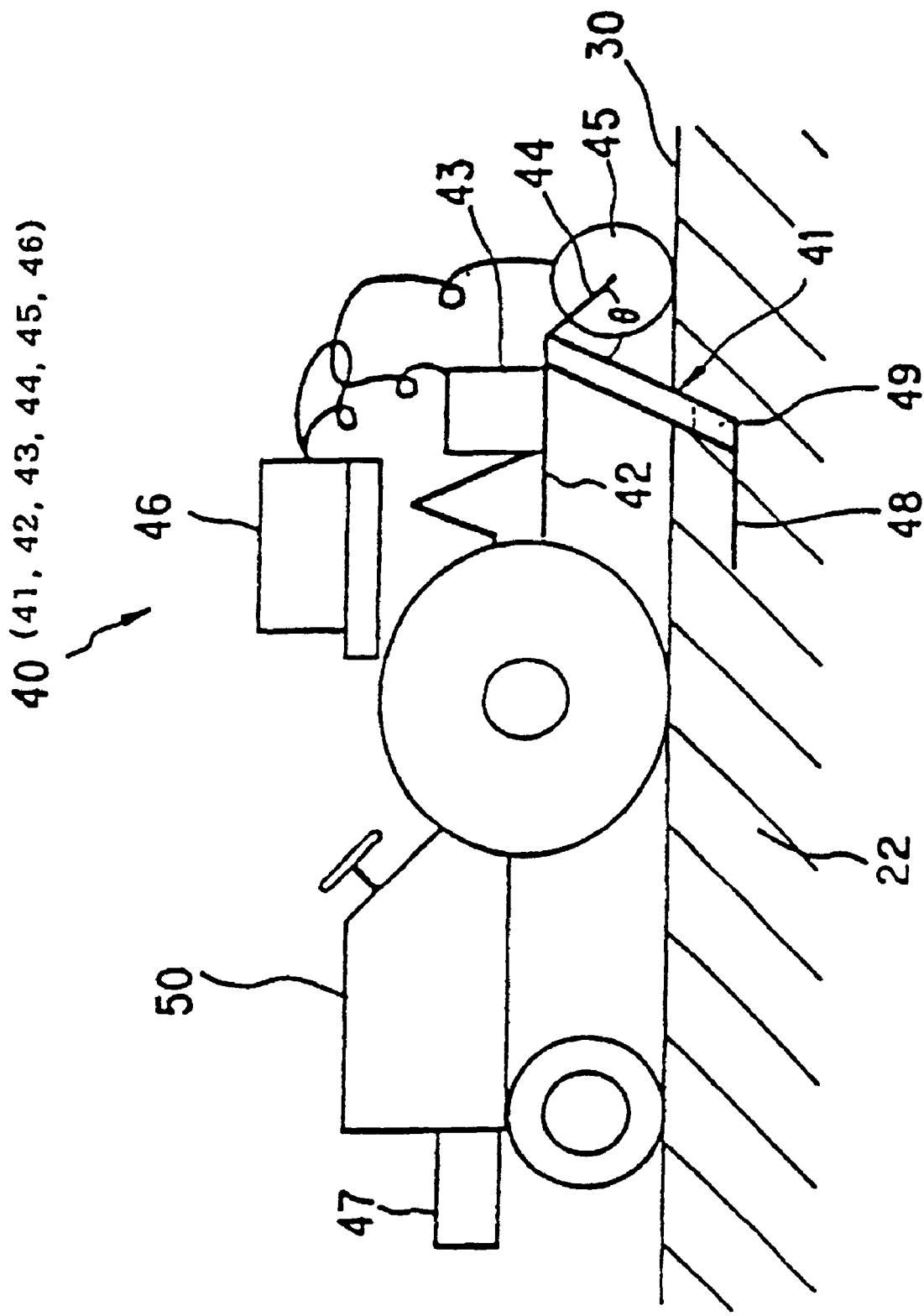
FIG. 2 is a rough sketch of an embodiment of an optical survey device to survey the optical characteristics of the soil in which this invention has been implemented.

FIG. 2 is a rough sketch of the device 40 to survey the optical characteristics of the soil which can be seen in FIG. 1. Optical soil survey device 40 is mounted on the rear of tractor 50, where it surveys the characteristics of soil 22.

Device 40 to survey the optical characteristics of the soil comprises plow-shaped main unit 41, whose forward extremity turns up soil 22; frame 42, which supports the sensor and connects tractor 50 and main unit 41; spectrometer 43, which is mounted on frame 42; wheel 45, which surveys the depth of the furrow and is connected to main unit 40 via arm 44; and survey control unit 46, which is mounted on tractor 50. Generator 47 is mounted on the front of tractor 50.

Main unit 41 has two parts, soil excavation unit 48, which goes under the surface of soil 22 and excavates it, and sensing unit 49, in the rear portion of unit 48, which collects the data.

Spectrometer 43 splits the light captured by sensing unit 49 into specific wavelengths.

Wheel 45, which surveys the depth of the soil surface, rotates automatically over the surface 30 of the ground. A rotary encoder or other device to detect angle of rotation (not pictured) is mounted at the point where the wheel connects to arm 44.

Survey control unit 46 comprises a personal computer or the like. It analyzes the data output by spectrometer 43.

Generator 47 is an AC generator which outputs 100 V AC.

Figure 3:
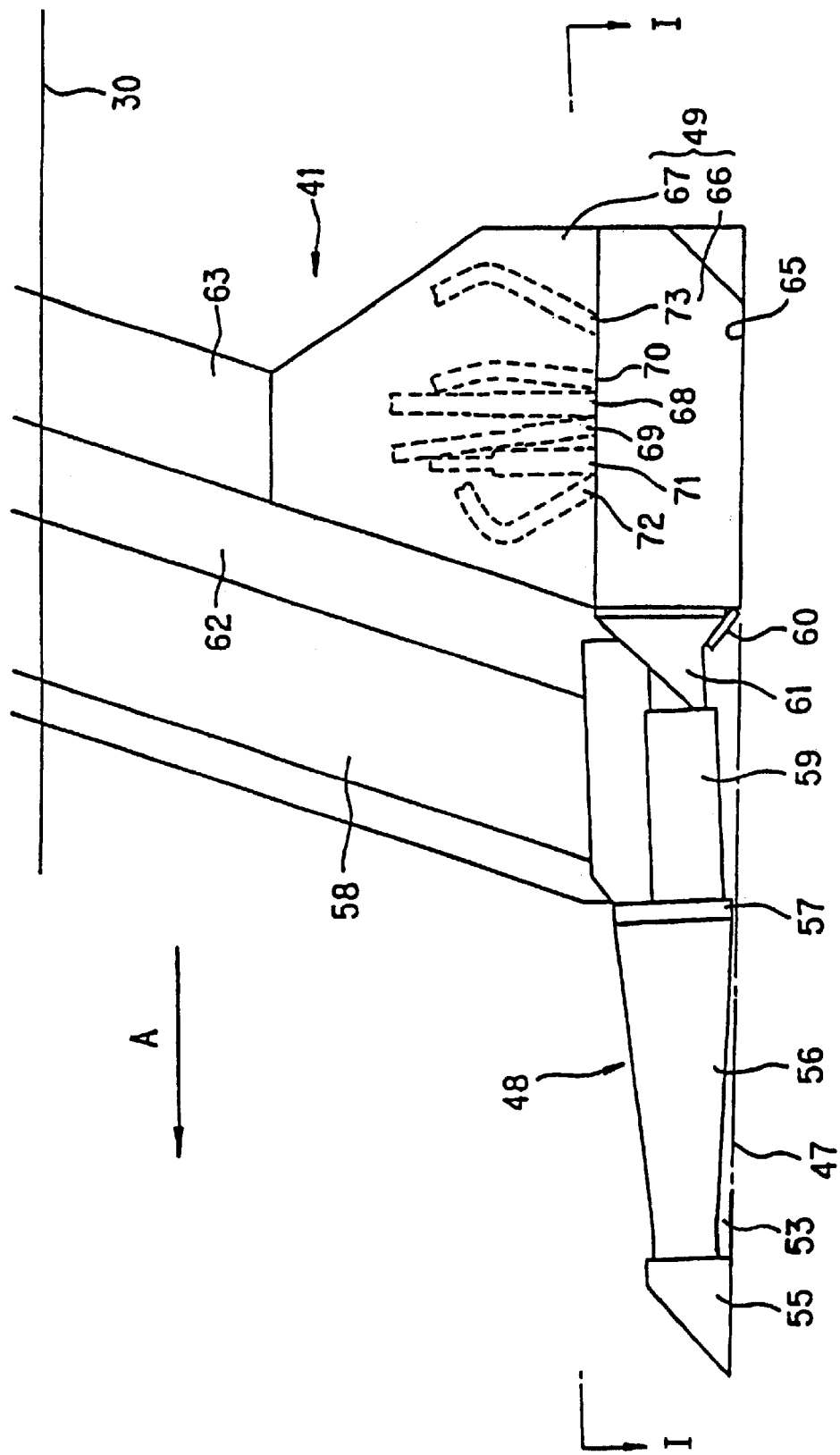
FIG. 3 is a lateral view of the excavation and sensing units which are below the main unit of the device pictured in FIG. 2.
Figure 4:
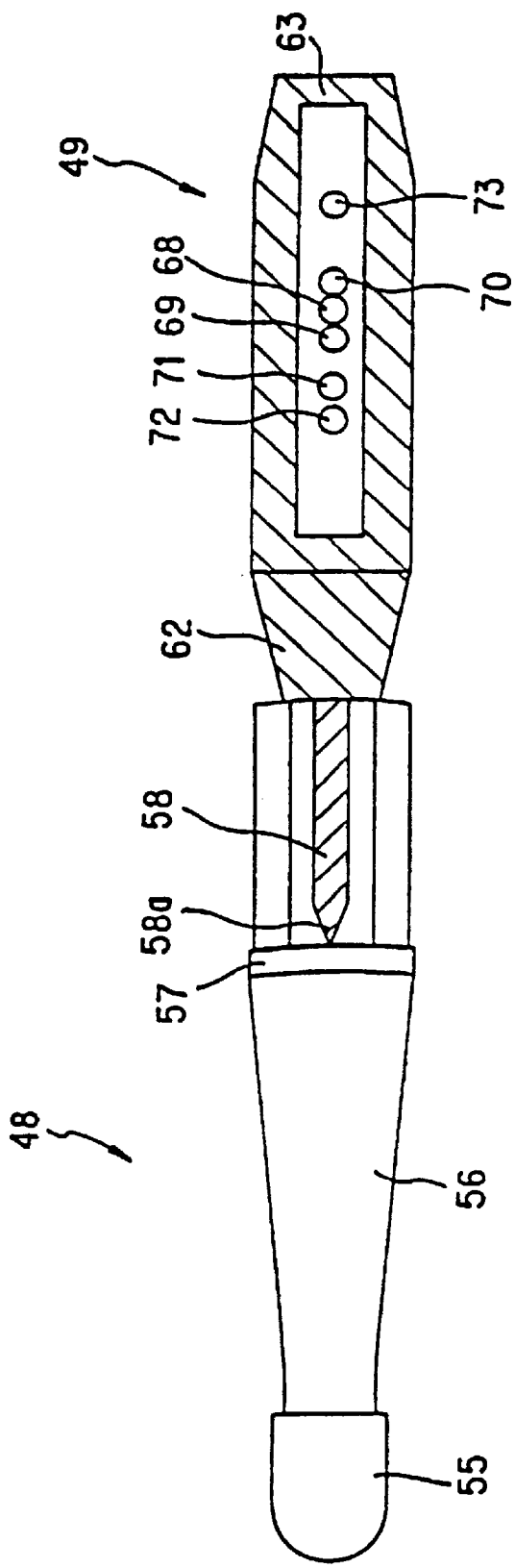
FIG. 4 is a cross section taken along line I—I in FIG. 3.

FIG. 3 is a partial lateral view of soil excavation unit 48 and sensing unit 49, both of which are below main unit 41. FIG. 4 is a cross section taken through line I—I in FIG. 3.

Soil excavation unit 48 turns up the soil as tractor 50 advances. It also creates a flat survey surface so that sensing unit 49 can easily survey the soil. Unit 48 travels through the soil parallel to ground surface 30.

Soil excavation unit 48 comprises penetration unit 55, a roughly conical piece with a tapered front end; penetration unit 56, a cylindrical piece with a gradually increasing cross section, which is connected to first penetration unit 55; penetration unit 59, which is connected to second penetration unit 56 via connector 57, and to whose upper portion is mounted shank 58, to be discussed shortly; and fourth penetration unit 61, which connects third penetration unit 59 to sensing unit 49, and to whose lower portion is mounted smoothing panel 60, to be discussed shortly.

Sensing unit 49 comprises sensing chamber 66, in which soil survey surface 65, which is the object of survey, is exposed; and housing 67, which contains multiple arrays of sensors. CCD camera 68, which captures an image of soil survey surface 65, the object of survey, is mounted in the center of housing 67. On either side of CCD camera 68 are optical fiber 69, which gathers visible reflected light, and optical fiber 70, which gathers near-infrared reflected light. Near optical fiber 69 is infrared-emitting thermometer (infrared thermocouple) 71, which surveys the temperature of the survey surface under observation. On two sides of housing 67 are optical fibers 72 and 73, which provide illumination.

Casing 63, which protects the cords for the fiber optics, extends upward from the top of sensing unit 49 at a slight angle opposite the direction of movement. Support 62 is provided between casing 63 and shank 58.

In this design, penetrating unit 55 on the front of soil excavation unit 48 is roughly conical, with a round cross section; penetrating unit 56, which is connected to unit 55, also has a round cross section. Thus as soil excavation unit 48 goes through the ground, it bores a round hole. The fact that it has a round cross section means that it experiences minimal resistance from the surrounding soil. This allows it to proceed smoothly through the soil so that it does not fail to obtain the soil characteristics which are the object of survey.

As discussed above, the tunnel excavated by penetrating unit 55 is cylindrical. The bottom of this cylinder (i.e., the deepest portion) is therefore not flat, but describes an arc. As can be seen in FIG. 3, penetrating units 56, 59, and 61 are all placed above line 47, which links the bottoms of penetrating unit 55 and sensing unit 49, leaving a space 53 between the ground and the second penetration unit 56 (under the second penetration unit 56 and behind the first penetration unit 55). Thus the floor of the excavated tunnel (i.e., its deepest portion) remains unaffected by the intermediate penetrating units and keeps its rounded shape up to the front of sensing unit 49.

However, if this curved survey surface were to be the object of survey, it would not be possible to survey its characteristics accurately.

For this reason a smoothing panel 60 is mounted on the lower surface of the fourth unit, penetrating unit 61. This panel flattens the theretofore curved floor of the tunnel.

Figure 5A:
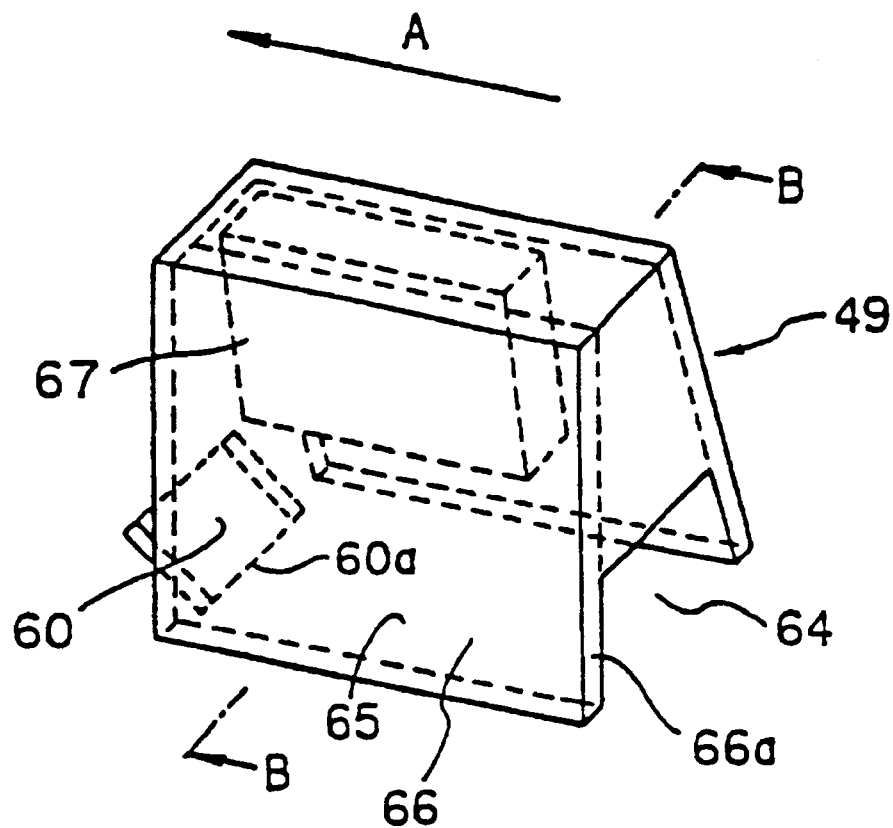
FIG. 5 illustrates the relative positions of the sensing unit and the smoothing panel.
Figure 5B:
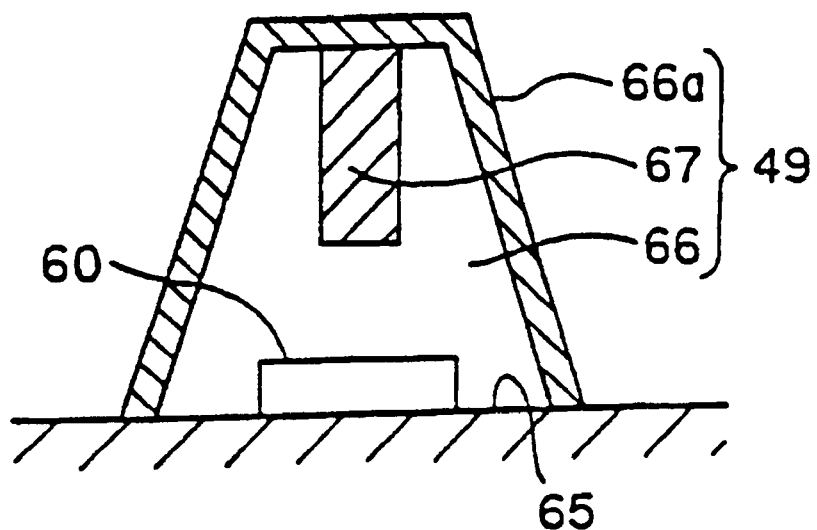

FIG. 5 illustrates the construction of sensing unit 49 and smoothing panel 60. FIG. 5A is a simplified perspective drawing; FIG. 5B is a cross section taken along line B—B in FIG. 5A. Sensing unit 49 is enclosed by casing 66*a*, which has the shape of a trapezoidal pedestal. Its interior forms sensing chamber 66. On the ceiling of this chamber is sensor housing 67.

The lower portion 60*a* of smoothing panel 60 is placed along the bottom surface of casing 66*a*. That is to say, it is placed at the height of soil survey surface 65. the object of survey. Panel 60 is mounted at an angle in direction of movement A.

Figure 6A:
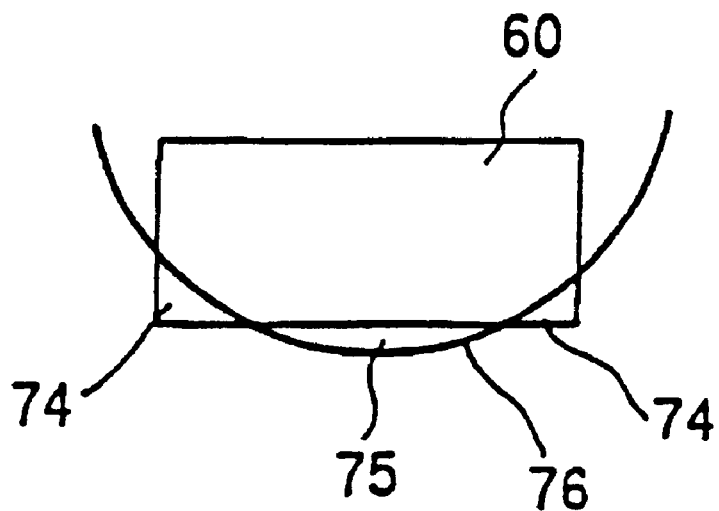
FIGS. 6A and 6B illustrate how the smoothing panel shown in FIG. 5 works.
Figure 6B:
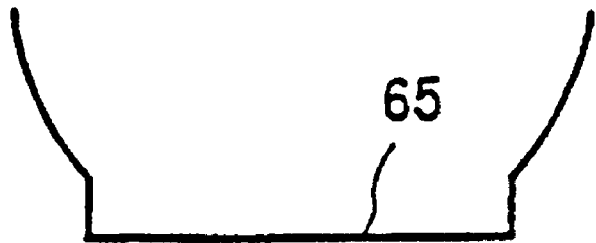

We shall explain the working of smoothing panel 60 with reference to FIG. 6. As can be seen in FIG. 6A, penetration unit 55 has bored a tunnel with a curved floor, which we shall call 76. After first penetration unit 55 has been forced through the surrounding soil, smoothing panel 60 scrapes away the soil from portions 74 and fills in portion 75 adjacent to this curved floor. This results in the flat soil survey surface 65 shown in FIG. 6B, which will be the subject of survey.

The fact that sensing unit 49 is able to use this flat soil survey surface 65 for its surveys insures the accuracy of the results.

As can be seen in FIG. 5A, there is an opening 64 in the lower portion of sensing unit 49 on the side opposite direction of travel A. This opening allows the soil which gets into sensing chamber 49 a means to escape. We shall discuss the action of this opening 64 presently.

Soil excavation unit 48 and sensing unit 49, which are below main unit 41, proceed below the soil. Shank 58, support unit 62 and protective casing 63 are above main unit 41; and as can be seen in FIG. 3, the portions of shank 58, support unit 62 and protective casing 63 which are below ground level 30 also proceed below the soil.

However, as is evident in FIG. 4. the cross section of shank 58, support unit 62 and protective casing 63 is quite narrow. When the device proceeds below the surface of the soil, it experiences minimal resistance from the surrounding soil.

As can be seen in FIG. 3, shank 58, which turns up the soil on the forward end of the device, is angled slightly away from direction of movement A so as to minimize the resistance it experiences as it moves forward. As can be seen in FIG. 4, a cross section of this shank in its longitudinal dimension reveals it to be long and narrow, with tip 58*a* having a pointed end angled at perhaps 30°. This allows the device to experience only minimum resistance as it proceeds below the ground so that it can survey the characteristics of the soil at an appropriate depth.

In this embodiment, soil survey surface 65, where the survey is to be made, can lie at a depth anywhere between 15 and 35 cm below the ground. The depth of survey surface 65 can be changed by raising or lowering the wheels (not pictured) on either side of support frame 42. The depth of survey can be ascertained by surveying the angle ($\theta$ in FIG. 2) between shank 58 and support arm 44. Angle $\theta$ is detected by a rotary encoder or other device to detect angle of rotation which is mounted where support arm 44 connects to wheel 45.

In this embodiment, the optical characteristics of the soil are surveyed as shank 58 turns it up. As shank 58 turns up the soil, the surrounding soil is piled up and a long, narrow furrow is created.

Since this furrow can serve as a conduit for stray light, it must be covered immediately. If the survey is performed on a relatively deep soil survey surface, the furrow will be filled in naturally by the soil on either side, so there is no particular problem. If it is performed on a shallow soil survey surface, however, it is crucial to cover the furrow.

To address this problem, the present embodiment has a mechanism to fill the furrow in order to prevent any stray light from entering the survey chamber.

Figure 7A:
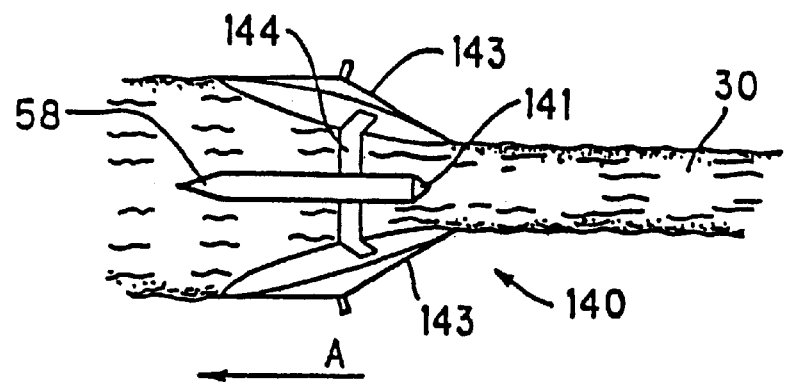
FIGS. 7A–7C show the configuration of the mechanism to refill the furrow in order to prevent stray light from getting into the survey chamber.
Figure 7B:
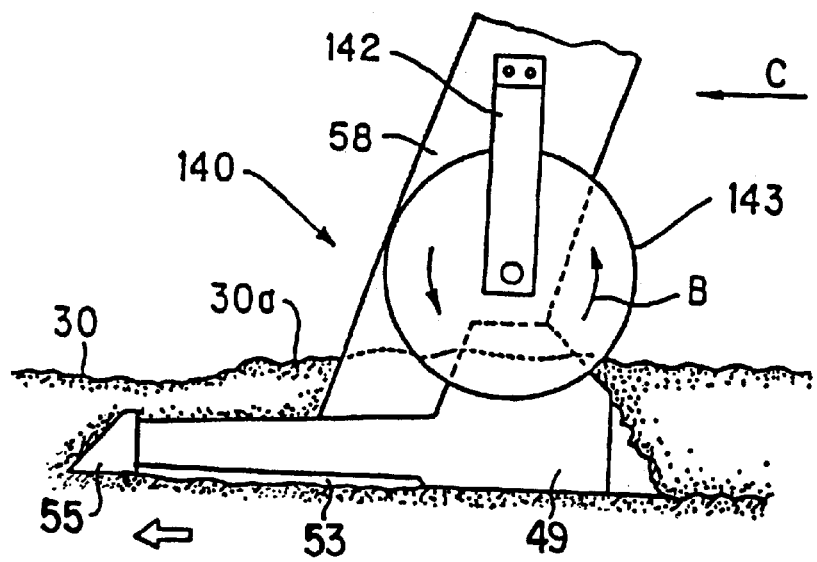
Figure 7C:
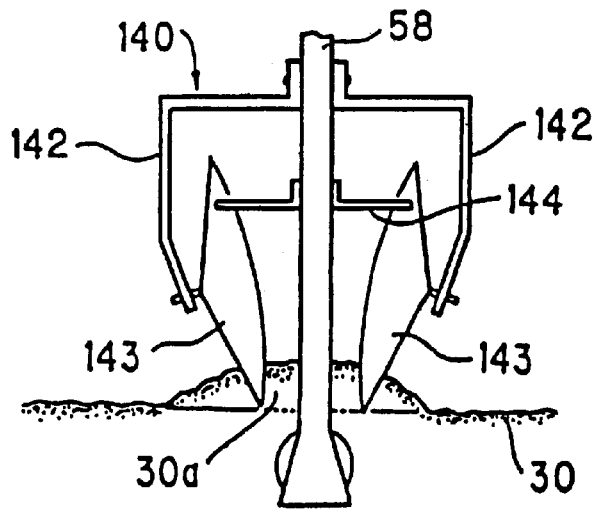

FIG. 7 shows a mechanism to refill the furrow. FIG. 7A is a plan view of mechanism 140; FIG. 7B is a lateral view; FIG. 7C is a lateral view as seen from direction C in FIG. 7B.

As can be seen in FIG. 7A, shank 58 turns up soil survey surface 30 as it moves forward in direction A. As it proceeds, it leaves a furrow 141 in its wake.

Furrow filling mechanism 140 comprises two curved plows 143, which are mounted to shank 58 via support arms 142, and scraper 144, which is mounted directly on shank 58.

Curved plows 143 are mounted so that they rotate approximately level with the surface of the ground 30. As can be seen in FIG. 7A, they are mounted at an angle so that the wide track which proceeds the device in direction A is gradually compressed.

As is shown in FIGS. 7B and 7C, when shank 58 moves forward, it creates a row of heaped up soil 30a on the surface of the ground 30. To address this, curved plows 143 rotate in direction B as shank 58 proceeds. The rotation of these plows forces heaped up soil 30a inward and upward. The compressed soil is then pushed downward by scraper 144. Thus the furrow 141 created by shank 58 is filled in and stray light is prevented from entering the survey chamber.

Figure 8A:
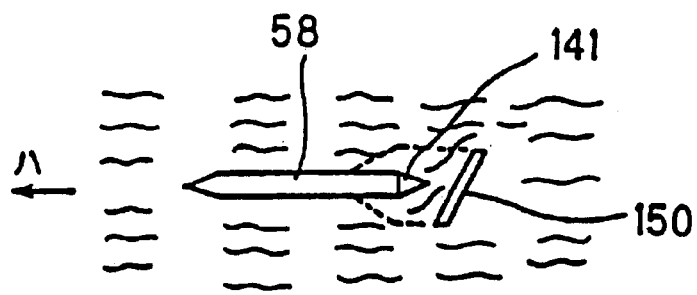
FIGS. 8A–8C show the configuration of another mechanism to refill the furrow in order to prevent stray light from getting into the survey chamber.
Figure 8B:
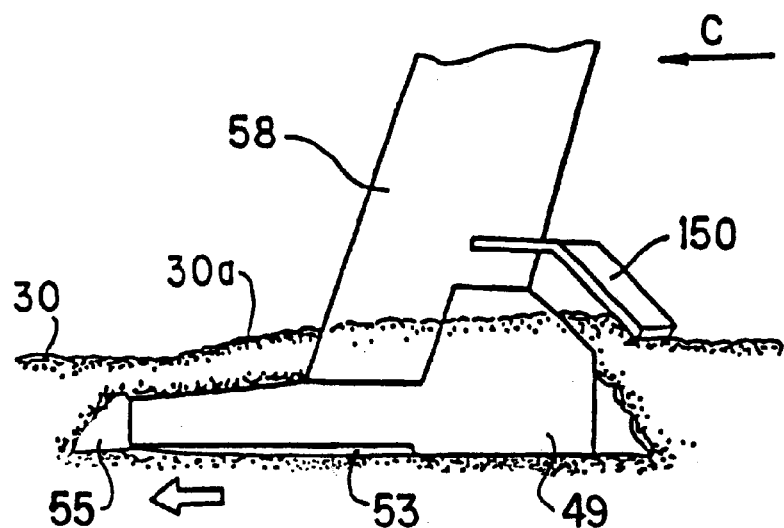
Figure 8C:
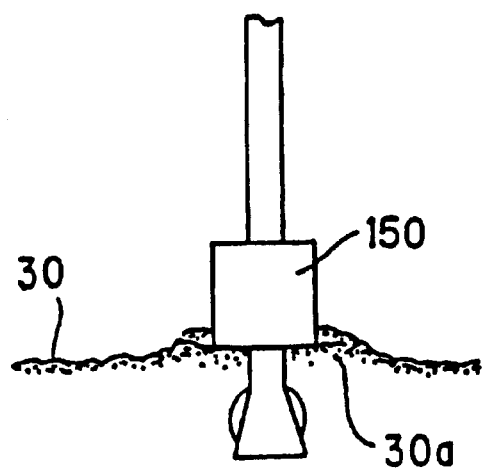

FIG. 8 shows another mechanism to fill the furrow. FIG. 8A is a plan view of furrow filling mechanism 150; FIG. 8B is a lateral view; FIG. 8C is a lateral view as seen from direction C in FIG. 8B.

As can be seen in FIG. 8B, mechanism 150 comprises a flat panel which is bent into an L shape and mounted on the rear portion of shank 58. As can be seen in FIG. 8(a), it is mounted obliquely with respect to direction of movement A.

As shank 58 goes forward, the heaped up soil 30a turned up from below is scraped away and the furrow 141 created by shank 58 is refilled so that no stray light can enter the survey chamber.

As can be seen in FIG. 8A, mechanism 150 is mounted obliquely with respect to the direction A in which the device is moving. This is to minimize the resistance it experiences from the soil.

As can be seen in FIGS. 7B and 8B, after first penetration unit 55 is forced through the surrounding soil to form a tunnel, pressure of the surrounding soil can release into space 53 before sensing unit 49 is passed over the smoothed bottom of the tunnel. (Note: pressure of the surrounding soil is supported at page 31, line 2 from bottom of page.)

Figure 9A:
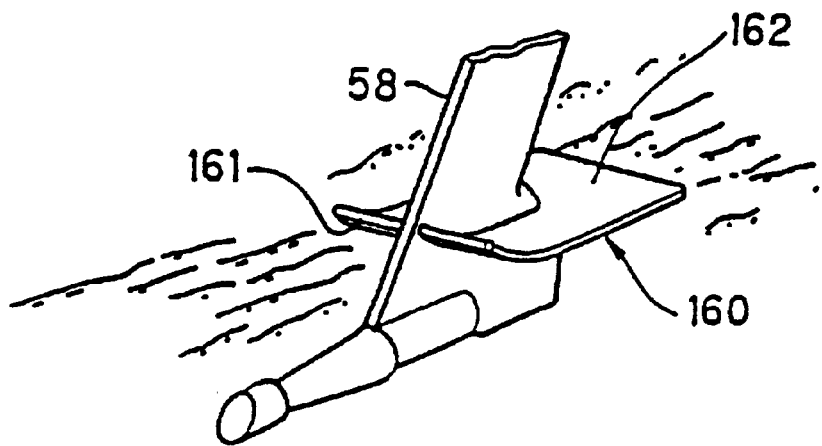
FIGS. 9A and 9B show the configuration of a lightproof sheet which is a means to block stray light.
Figure 9B:
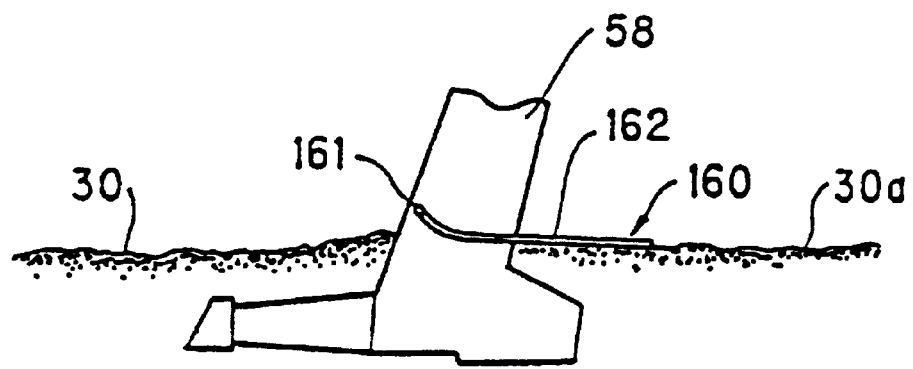

Instead of a mechanism to refill the furrow, FIG. 9 shows a lightproof sheet which is another means to block stray light. FIG. 9A shows the entire lightproof sheet 160. FIG. 9B shows a lateral view.

As can be seen in the drawings, lightproof sheet 160 is mounted to shank 58 in such a way as to cover the surrounding area.

Lightproof sheet 160 comprises supports 161, plastic rods or the like mounted to shank 58 slightly above the level of the ground 30, and sheet 162, made of rubber or some other opaque material, which is mounted to supports 161.

As lightproof sheet 160 moves forward, it covers the furrow (furrow 141 in FIGS. 7 and 8) with sheeting 162. Thus stray light is prevented from entering the survey chamber.

Optical soil survey device 40 surveys the optical characteristics of the soil by using spectrometer 43 and survey control unit 46 to analyze the data gathered by sensing unit 49. However, the presence of other equipment in the vicinity or changes in the properties of the light source over time may cause the optical responses of device 40 to vary slightly.

Figure 10:
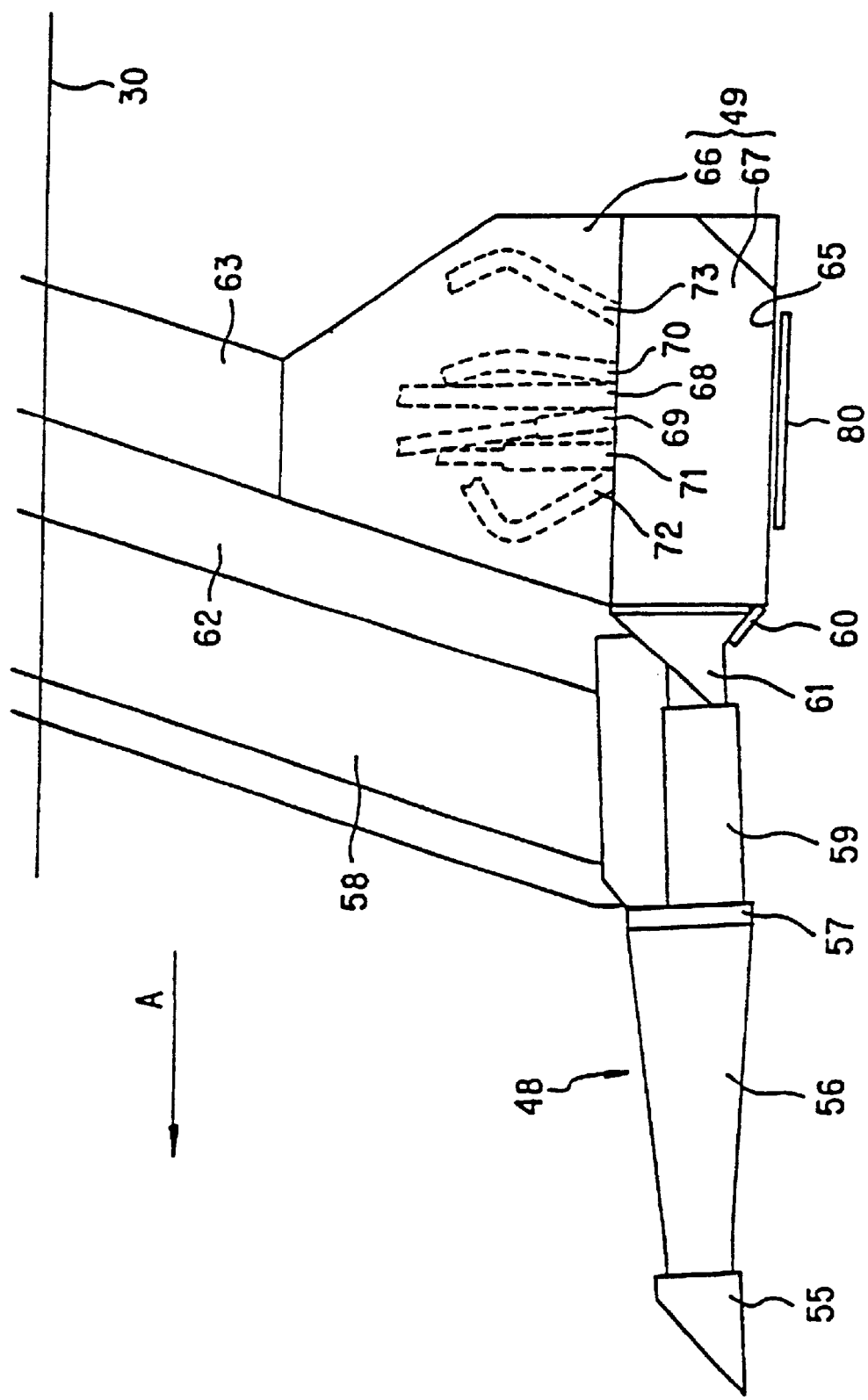
FIG. 10 illustrates how the reflectance under illumination (R) and in the dark state (D) are recorded at the start of the survey by attaching a reflector plate below the sensing unit at the level where the survey is made.

To address this problem, this embodiment uses a reflector plate 80 as illustrated in FIG. 10. At the start of the procedure and before the device is put into the ground, this plate is mounted with mounting hardware or the like (not pictured) below sensing unit 49 at the level where the survey is made (i.e., the level of soil survey surface 65). Using this plate, the reflectance under illumination (R) and the reflectance in the state of darkness (D) are recorded. Reflector plate 80 is then removed. Subsequent surveys of reflectance below ground are based on these recorded values. The processing scheme used for this will be discussed later.

Figure 11:
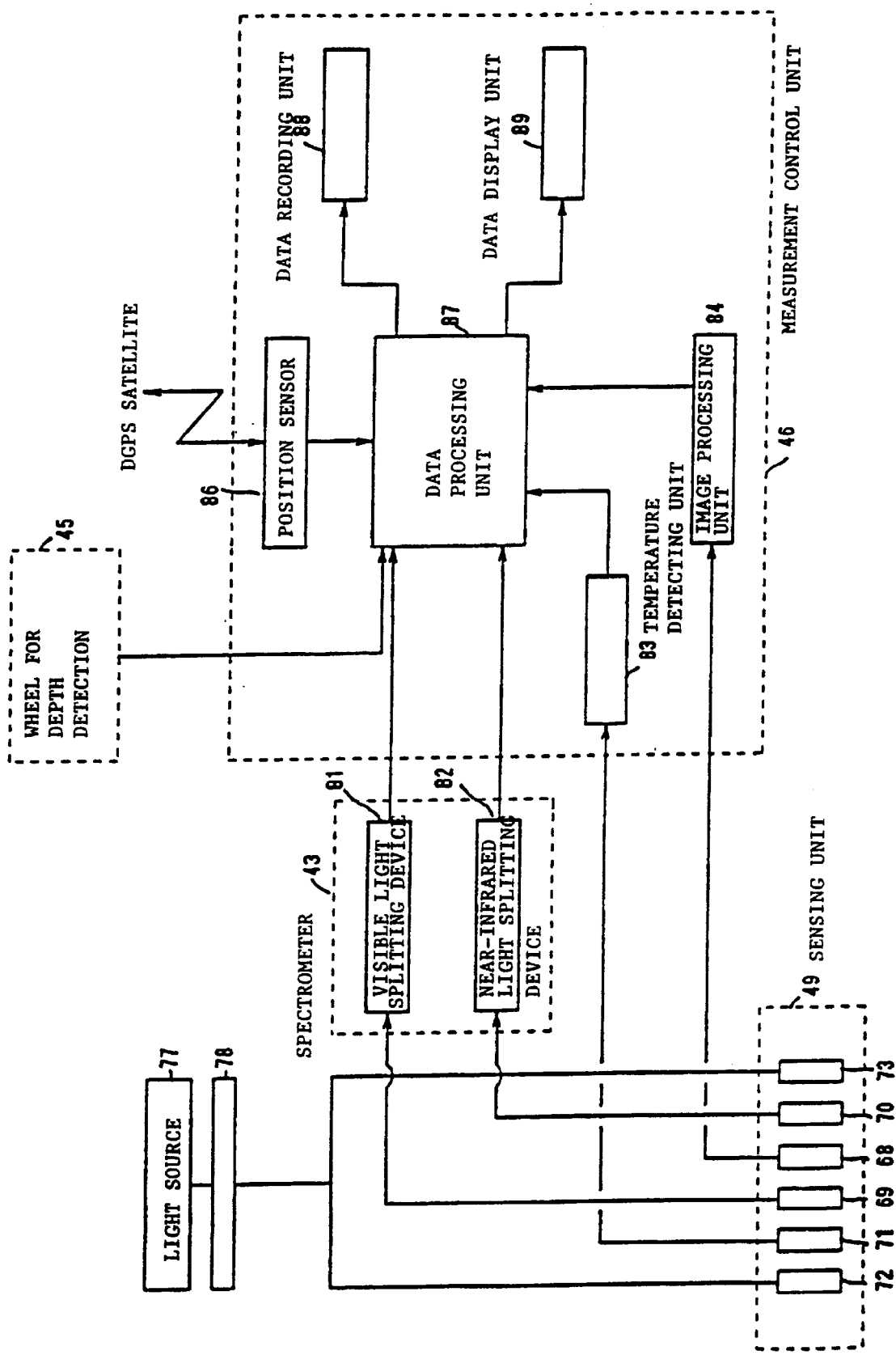
FIG. 11 is a block diagram of the electrical configuration of the device shown in FIG. 2.

We shall next discuss the electrical configuration of this embodiment with reference to FIG. 11. In FIG. 11 we see that optical soil survey device 40 comprises sensing unit 49, which receives the light from light source 77 and thereby senses the characteristics of the soil; spectrometer 43, which splits the visible and near-infrared reflected light in the data gathered by sensing unit 49; wheel 45, which detects the depth at which the soil characteristics are surveyed; and control unit 46, which controls the general operation of the device.

Light source 77 is a halogen lamp or the like. It supplies light to optical fibers 72 and 73, which illuminate sensing unit 49.

A shutter 78 is mounted on the front surface of light source 77. This shutter is used in the reflectance survey discussed earlier. At the start of the procedure, before the device is put into the ground, reflector plate 80 is mounted to the bottom of sensing unit 49 at the level where the survey is to be made (See FIG. 10). The reflectance under illumination (R) and the reflectance in the state of darkness (D) are then recorded. The shutter is used to produce a state of illumination or darkness.

More specifically, the area around where reflector plate 80 is mounted below sensing unit 49 is covered with a black cloth to mimic the appearance of the soil. A state of illumination is achieved by opening shutter 78; a state of darkness is achieved by closing it. In each state, the reflectance is surveyed.

Sensing unit 49 comprises CCD camera 68, which captures a color image of soil surface 65, the object of survey; optical fiber 69, which gathers visible reflected light; optical fiber 70, which gathers near-infrared reflected light; infrared-emitting thermometer (infrared thermocouple) 71, which surveys the temperature of the survey surface under survey; and optical fibers 72 and 73, which illuminate the chamber.

Of the light emitted by light source 77, optical fibers 72 and 73 transmit only that of a wavelength in the region between 400 and 2400 nm, including light between 400 and 900 nm, which includes the region of visible wavelength, and light between 900 and 1700 nm, which is the region of near-infrared wavelength.

Optical fiber 69, which gathers visible light, gathers the light in the region between 400 and 900 nm, which includes the region of visible wavelength, from the reflected light originally emitted by optical fibers 72 and 73.

Optical fiber 70, which gathers near-infrared light, gathers the light in the region between 900 and 1700 nm, which is the region of near-infrared wavelength.

Spectrometer 43 comprises visible light splitting device 81, which splits visible light, and near-infrared light splitting device 82, which splits near-infrared light. The light reflected off the soil survey surface which is gathered by optical fiber 69 is transmitted to device 81. The light reflected off the soil survey surface which is gathered by optical fiber 70 is transmitted to device 82. The intensity of the signal in each region is surveyed.

Devices 81 and 82 are both multichannel spectrometers with a linear array of photodiodes. 256 channels simultaneously detect light in the visible region, between 400 and 900 nm in wavelength; 128 simultaneous channels detect light in the near-infrared region, between 900 and 1700 nm; all detect light at high speed.

Survey control unit 46 comprises a personal computer or the like. It has a temperature detection unit 83, an image processing unit 84, a position sensor 86, a data processing unit 87, a data recording unit 88 and a data display unit 89.

Temperature detection unit 83 receives the output of infrared-emitting thermometer (infrared thermocouple) 71 and so detects the temperature of soil survey surface 65.

Image processing unit 84 receives the output of CCD camera 68, which has captured an image of soil survey surface 65. It processes the image data and determines their reliability.

Figure 12:
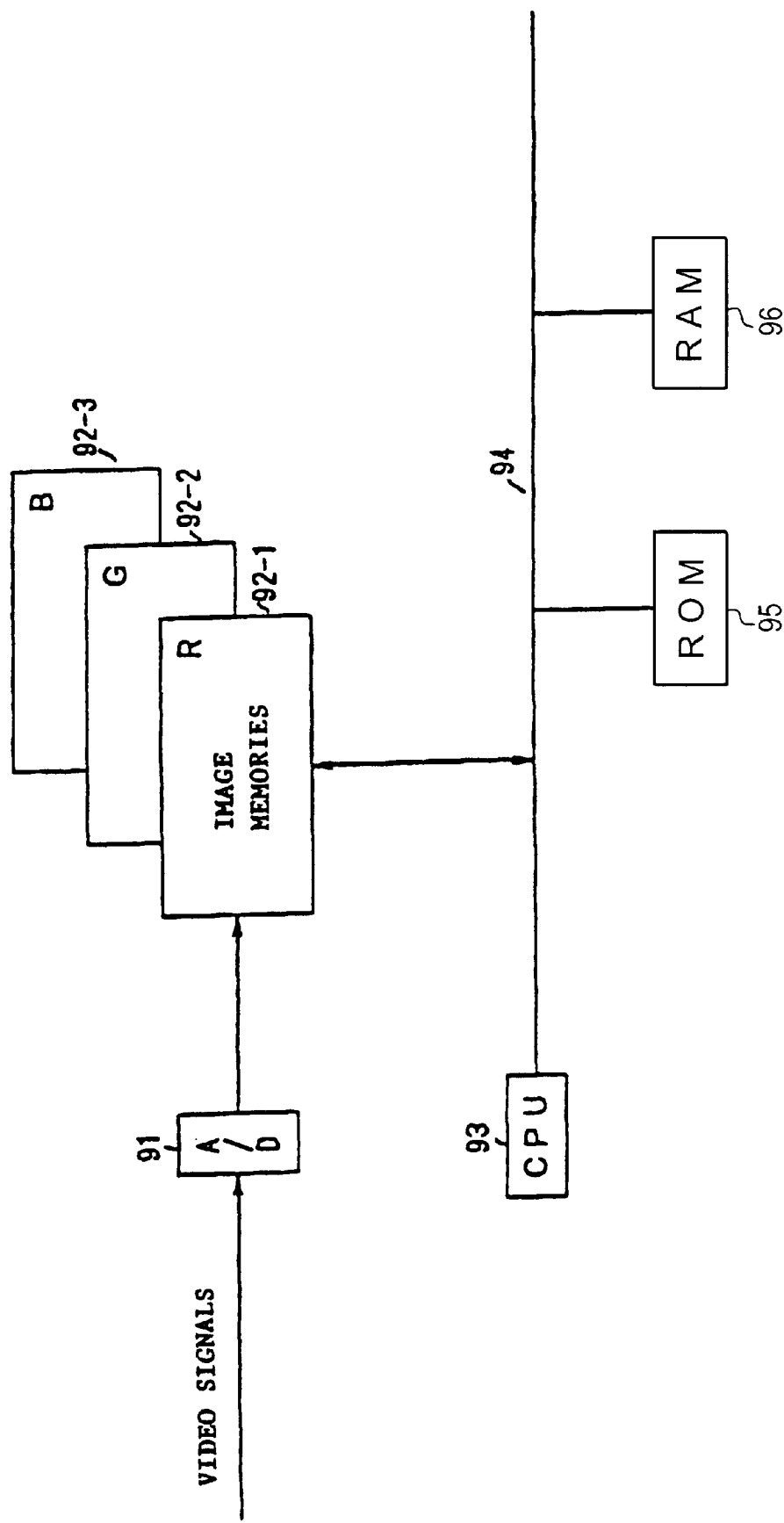
FIG. 12 is a block diagram of the configuration of the image processing unit shown in FIG. 11.

FIG. 12 is a block diagram of image processing unit 84. Image processing unit 84 comprises A/D converter 91, which digitizes the video signal transmitted by CCD camera 68; R image memory 92-1, G image memory 92-2 and B image memory 92-3, which respectively store the red (R), green (G) and blue (B) image data comprising the digitized video signal; CPU 93, which controls the general operation of the device; and ROM 95 and RAM 96, which are connected to the control bus 94 which goes to CPU 93.

Figure 13:
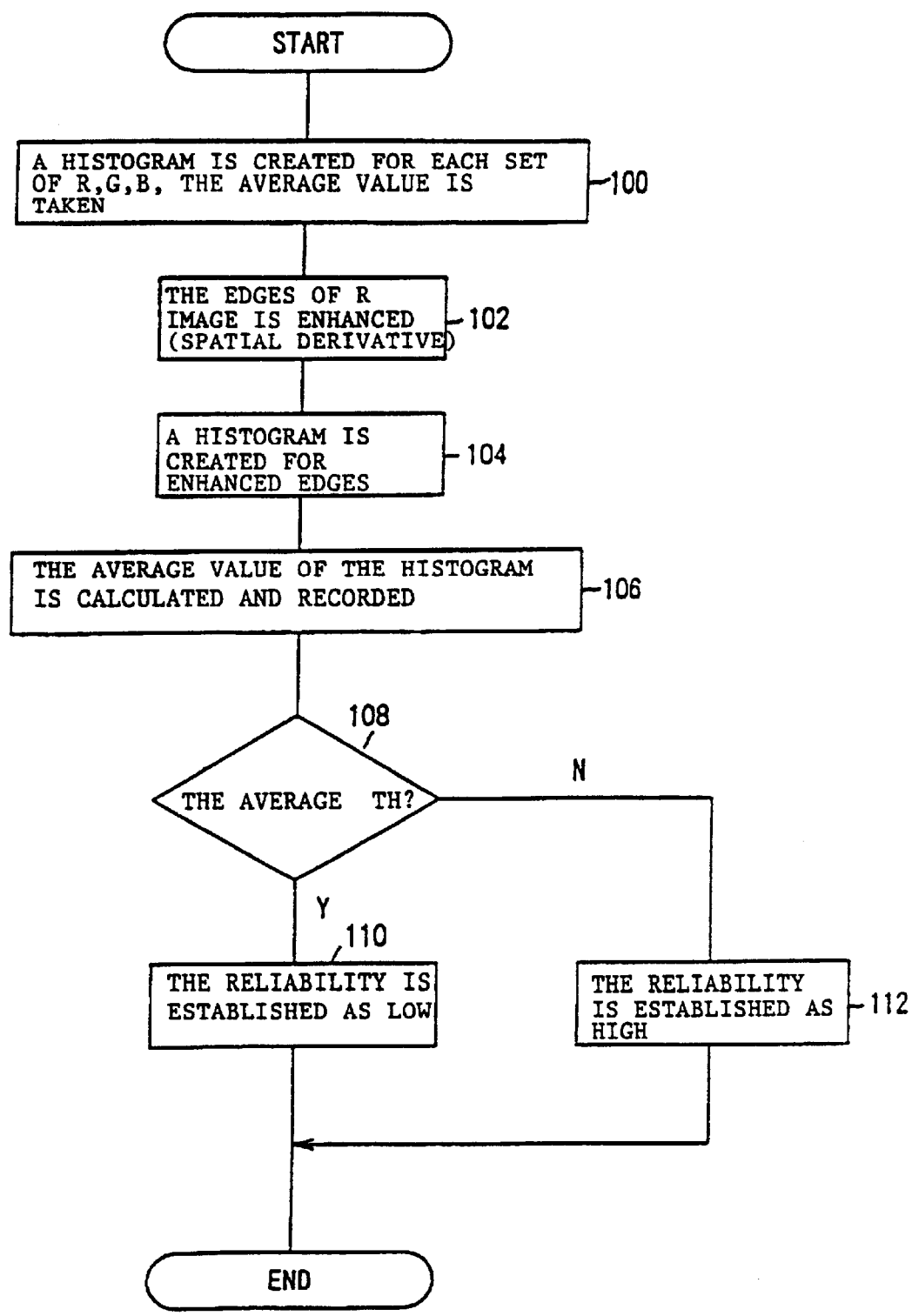
FIG. 13 is a flowchart of the routine the image processing unit executes to process the image data and the routine it executes to determine the reliability of that data.

FIG. 13 is a flowchart of the processes executed by CPU 93 in processing the image data and determining their reliability.

In this processing, a histogram is created for each set of R, G and B image data stored in image memories 92-1, 92-2 or 92-3, and the average value is taken (Step 100). In the processing which follows, as was discussed above, only the R portion of the processed image data will be used; however, the image data obtained in Step 100 will be used later when image processing unit 87 executes a routine to survey the soil characteristics.

In Step 102, a spatial derivative of the R image generated in Step 100 is performed and processing is executed to enhance the edges of the image data. A histogram is created with the enhanced edges (Step 104). The average value of the histogram is calculated and stored as data representing soil composition (Step 106).

If the edges of the image data have a high intensity, the survey surface of the soil which was imaged is too irregular, and the soil is not a suitable candidate for survey.

It is then determined whether the average value is greater than threshold value TH (Step 108). If it is (if the answer in Step 108 is "yes"), it is established that the reliability of the image data is low (Step 110). If the average value is below threshold value TH (if the answer in Step 108 is "no"), it is established that the reliability of the image data is high (Step 112). The result of this inquiry will be used later when data processing unit 87 executes a routine to survey the characteristics of the soil.

The reliability of the data can be detected by other method. When the surface of the field is uneven, it is not possible to measure the optical characters of the soil correctly. This unevenness is often coursed when the surface is cut roughly or when the penetration unit 55 is headed lower than the average plate 60. The distance between the surface of the soil and the optical devices, specially the sensors then becomes longer than it should be, and the accuracy of the measurement will be lowered.

Figure 22:
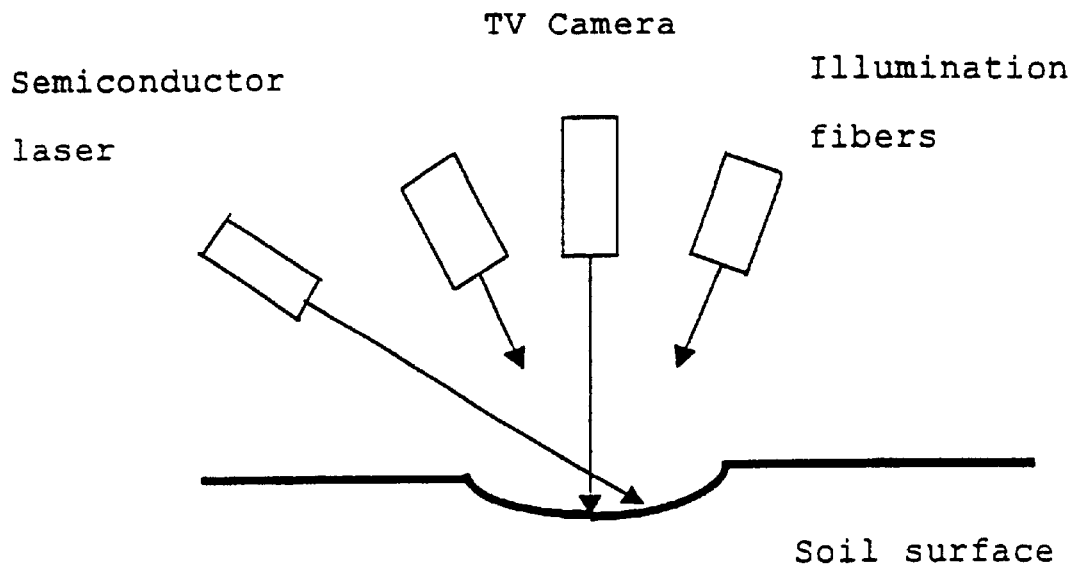
FIG. 22 illustrates a configuration to detect the unevenness of the soil surface.

In order to detect the unevenness of the soil surface, in this invention, the slit beam is shot toward the oblique direction to the soil surface by the semiconductor laser as shown in FIG. 22, and toward the perpendicular direction to the advancing direction. A TV camera observes the slit beamed surface of the soil. When the surface is uneven, the center of the slit beam will move from the center of the image taken by the TV camera. From this movement, the unevenness of the surface can be detected (this is called as a beam intercept method).

Figure 23:
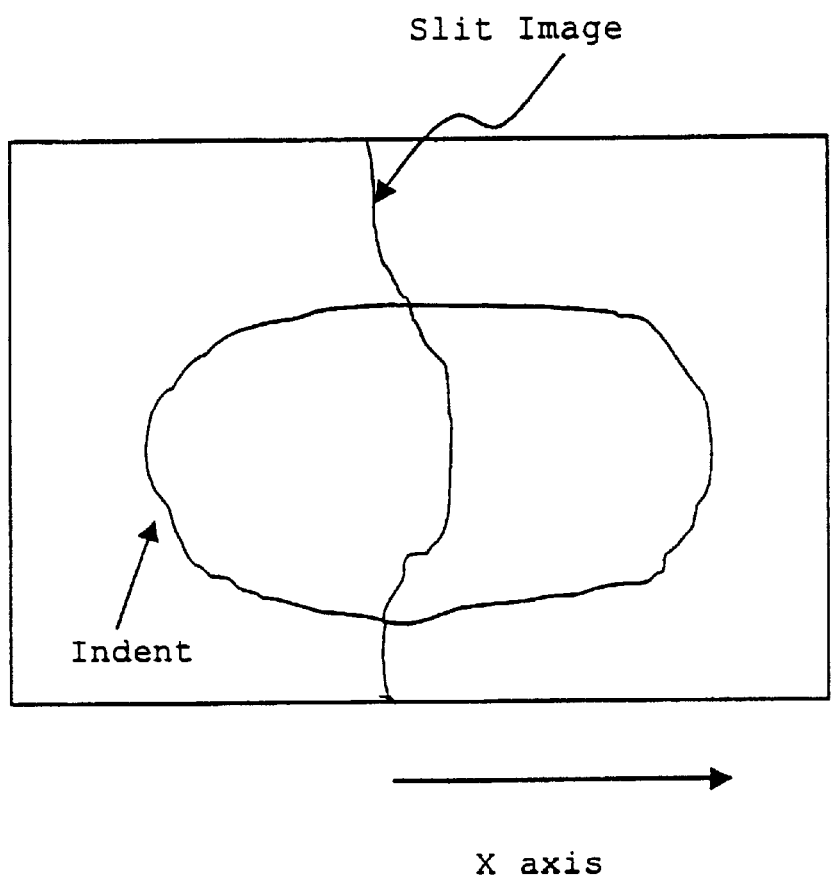
FIG. 23 illustrates a slit beamed image around an indent on the soil surface.
Figure 24:
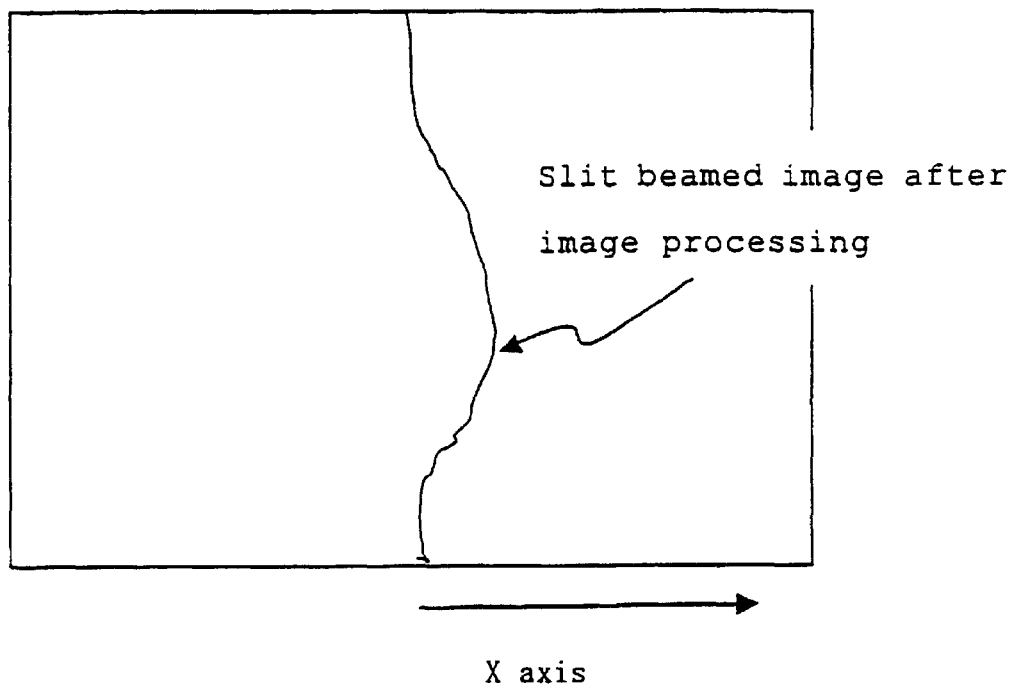
FIGS. 24(a) and (b) illustrate the slit beamed image after the image processing and the graph showing the relation between the X axis and the total number of pixels.
Figure 24:
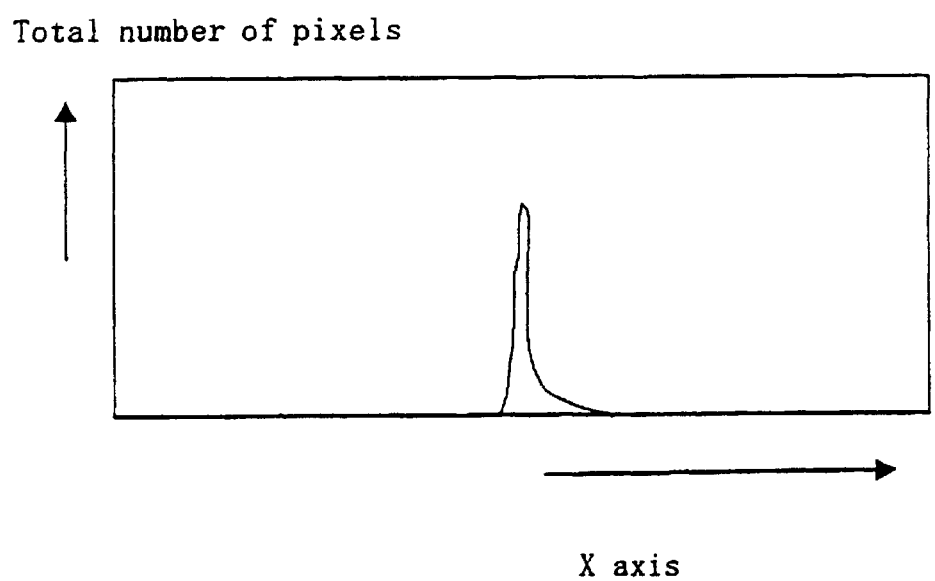
Figure 25:
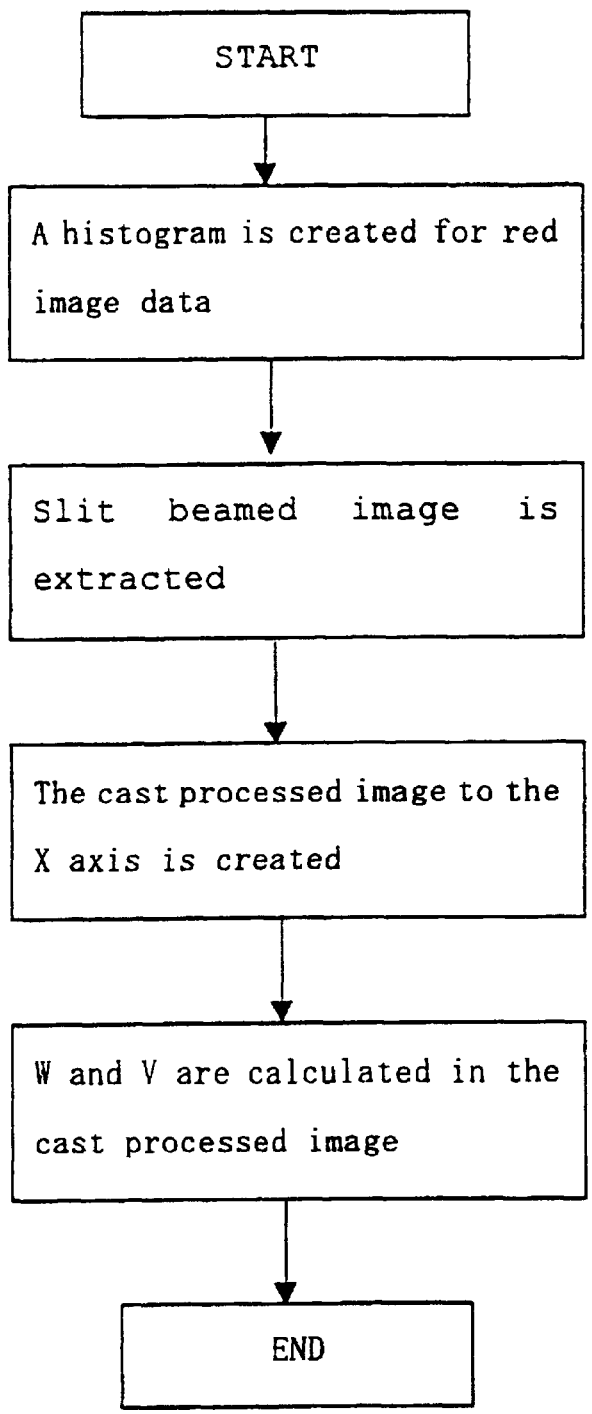
FIG. 25 illustrate a flowchart of detecting the evenness of the soil surface.

FIG. 23 shows the principle how to detect the unevenness of the soil surface. Since the soil surface shot by the slit beam is brighter than other portion, the slit image is obtained as shown in FIG. 24(*a*) by a conventional image processing. FIG. 24(*a*) shows a reflection image shot by a red laser beam. In this figure, the advancing direction is shown by X axis. The FIG. 24(*b*) is a cast processed image to the X axis of the reflection image. From this cast processed image, the center axis W, and the variance V can be obtained. The W shows the average depth of the soil surface, and the V shows the evenness of the soil. From these two data, the characteristics of the soil surface can be detected. if the value of W and V exceed the predetermined levels, the image data measured by this device can be invalid to keep the measurement data reliable. The values of W and V can be used to detect the evenness and viscoelasticity of the soil surface. From the evenness of the soil surface, the measurement data can also be corrected. FIG. 25 shows the flow chart of detecting the evenness of the soil surface mentioned above.

To return once more to our discussion of FIG. 11, position sensor 86 obtains data representing the current position of survey device 40 via a signal from DGPS satellite 14.

Data processing unit 87 surveys the characteristics of the soil based on data from device 81, which split the visible light, device 82, which split the near-infrared light, temperature detector 83, image processing unit 84, pulse generator 85 and position sensor 86.

Data storage unit 88 comprises a PC card or the like. It stores the survey data produced by data processing unit 87.

Data display unit 89 comprises a liquid crystal display or the like. It displays the survey data output by data processing unit 87.

In the explanation given earlier, it was stated that shutter 78 is used at the beginning of the survey process to create light and dark states. However, it would also be possible to use a round rotating panel with holes in it instead of shutter 78. The soil survey surface to be studied would then be irradiated repeatedly under light and dark conditions, and the intensity spectrum of the reflection surveyed in both states. The difference between the two would be obtained by data processing unit 87. This design would make it possible to correct for stray light.

Figure 14:
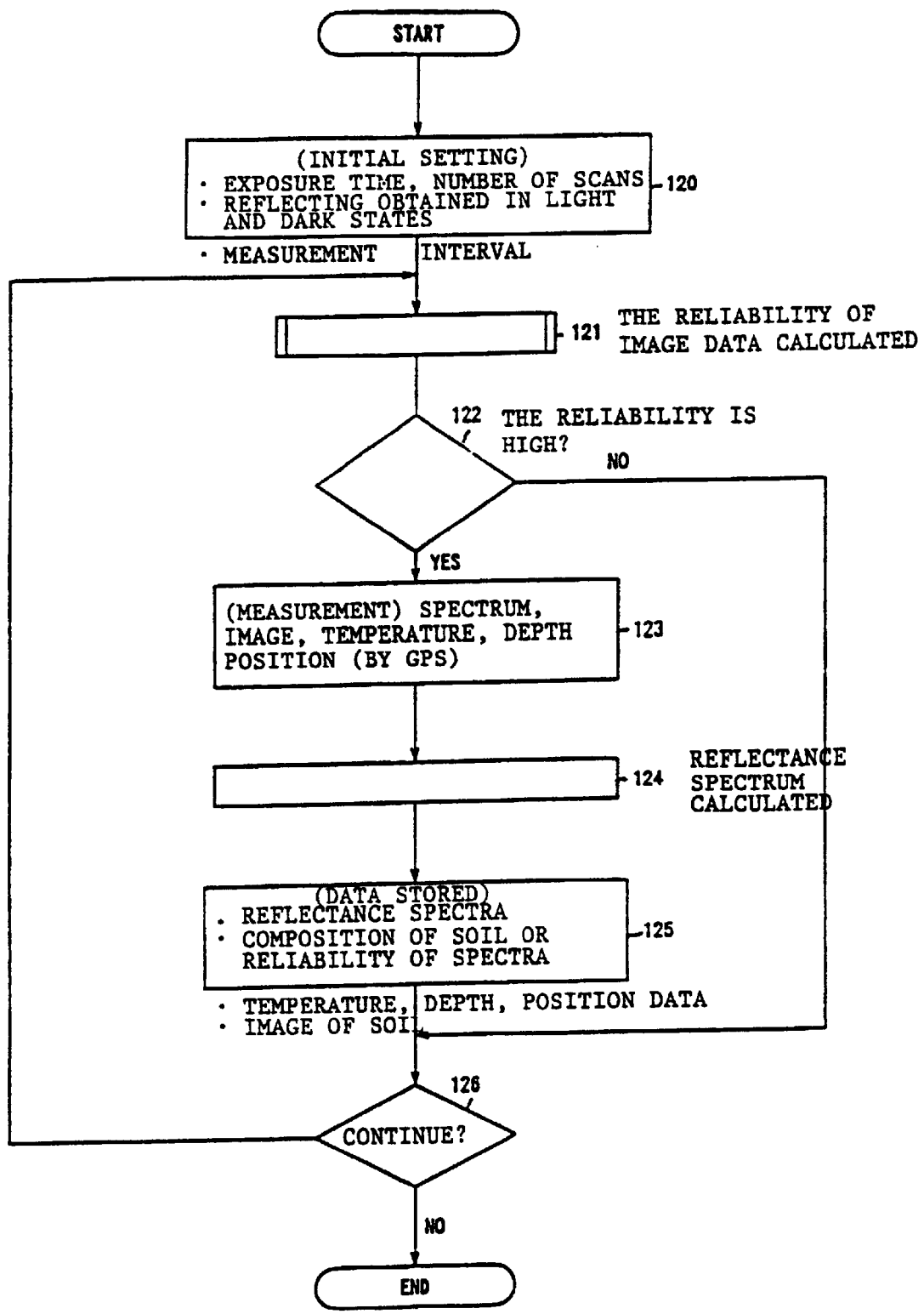
FIG. 14 is a flowchart of part of the routine executed by the data processing unit shown in FIG. 11 to survey the characteristics of the soil.

We shall next discuss, with reference to FIG. 14, the processing executed by data processing unit 87 to survey the characteristics of the soil. The processing in FIG. 14 is premised on the assumption that the vehicle is following a prescribed course.

First the initial settings are made. The intensity of the reflection is obtained in the light and dark state using reflector plate 80, as was explained with regard to FIG. 10. The exposure time, number of scans (cumulative number) and survey interval are determined (Step 120).

Next, the reliability of the image data is calculated (Step 121). This is the processing which was discussed above with reference to FIG. 13. The values established in Steps 110 and 112 are consulted.

It is determined whether the reliability of the image data is high (Step 122). If it is not (if the answer in Step 122 is "no"), we proceed to step 126. If the reliability of the data is high (if the answer in Step 122 is "yes"), the spectral data are surveyed by devices 81 and 82 in spectrometer 43, the image data are surveyed by image processing unit 84, the temperature data are surveyed by temperature detection unit 83, the depth data are surveyed by wheel 45; and the position data are surveyed by position sensor 86 (Step 123).

The reflectance spectrum is calculated based on these data (Step 124). For example, in the visible region, the range between 400 and 900 nm is surveyed. If D is the intensity of the signal when shutter 78 is closed and sensing chamber 67 is dark, R is the intensity of the signal when shutter 78 is open and sensing chamber 67 is lighted, and S is a sample value of the intensity of the signal, then the reflectance spectrum T is obtained by the following formula.

$$T = (S-D)/(R-D)$$

In the near-infrared region, the range surveyed is between 900 and 1700 nm. The same survey scheme is used as for visible light.

In Step 125, the data acquired in the preceding processing are stored. These include data representing the reflectance spectra, the composition of the soil, the reliability of the spectra (i.e., the reliability value obtained in Step 121), temperature, depth, position and the image of the soil.

Next it is determined whether surveying is to continue (Step 126). If it is (if the answer in Step 126 is "yes"), we return to Step 121. If surveying is completed (if the answer in Step 126 is "no"), the processing ends.

The question of whether surveying is to continue refers to whether the vehicle has completed its specified course or whether the number of points where the soil characteristics are to be surveyed has reached a given value, and is determined according to a previously established plan. If the plan has been fulfilled, surveying ends. A system abnormality will also cause surveying to end.

The data in Step 125 are stored in data storage unit 88. They might, for example, be transmitted to a personal computer by a scheme such as spectral diffusion.

Figure 17:
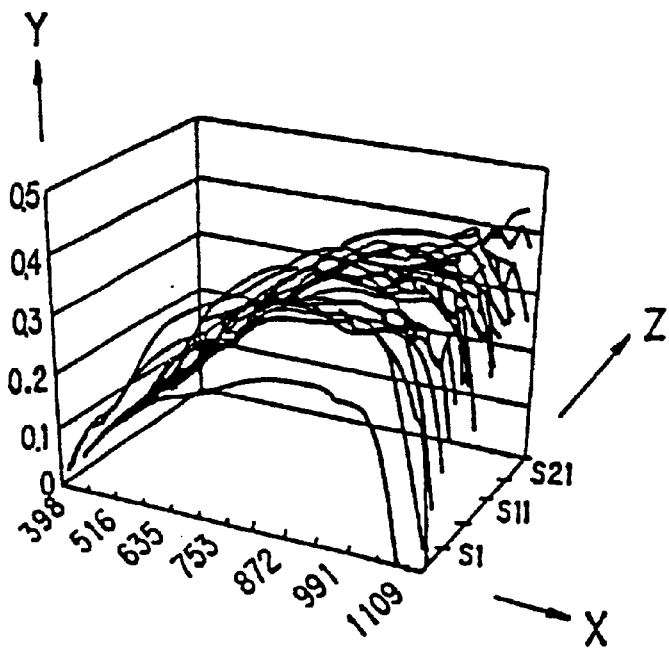
FIG. 17 illustrates the reflectance spectrum of visible light acquired by the processing in Step 126 of FIG. 14.
Figure 18:
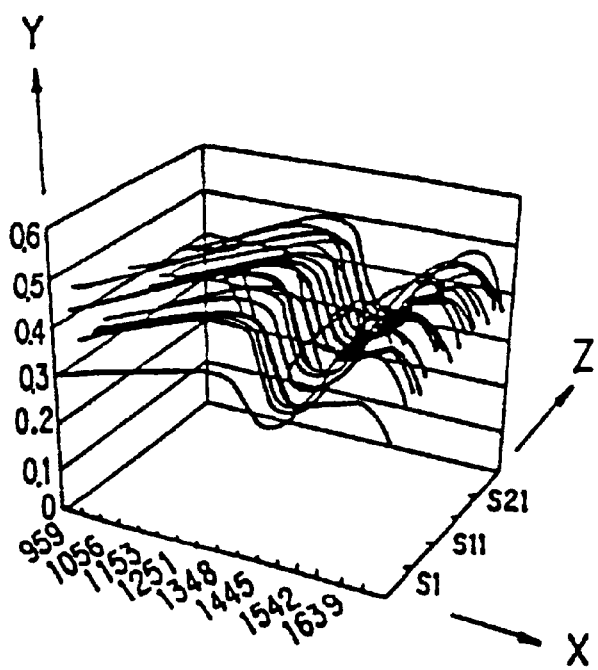
FIG. 18 illustrates the reflectance spectrum of near-infrared light acquired by the processing in Step 126 of FIG. 14.
Figure 19:
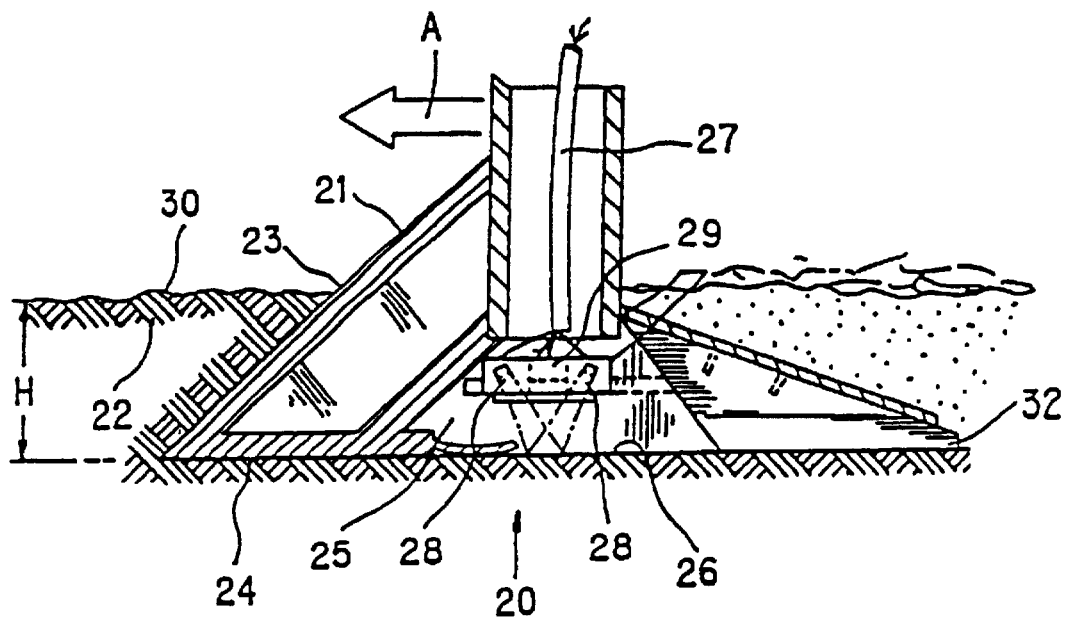
FIG. 19 is a cross section of the excavation and sensing portions of a prior art device to survey optical characteristics.
Figure 20:
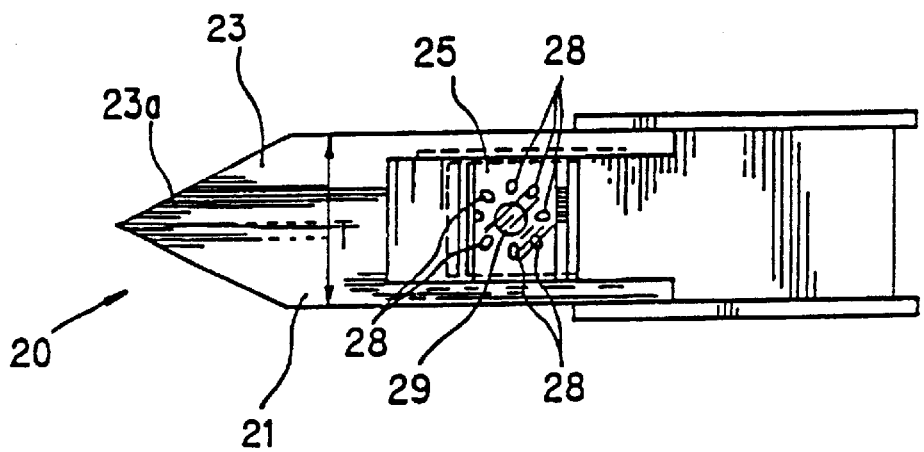
FIG. 20 is a view from underneath the device to survey optical characteristics shown in FIG. 19.
Figure 21:
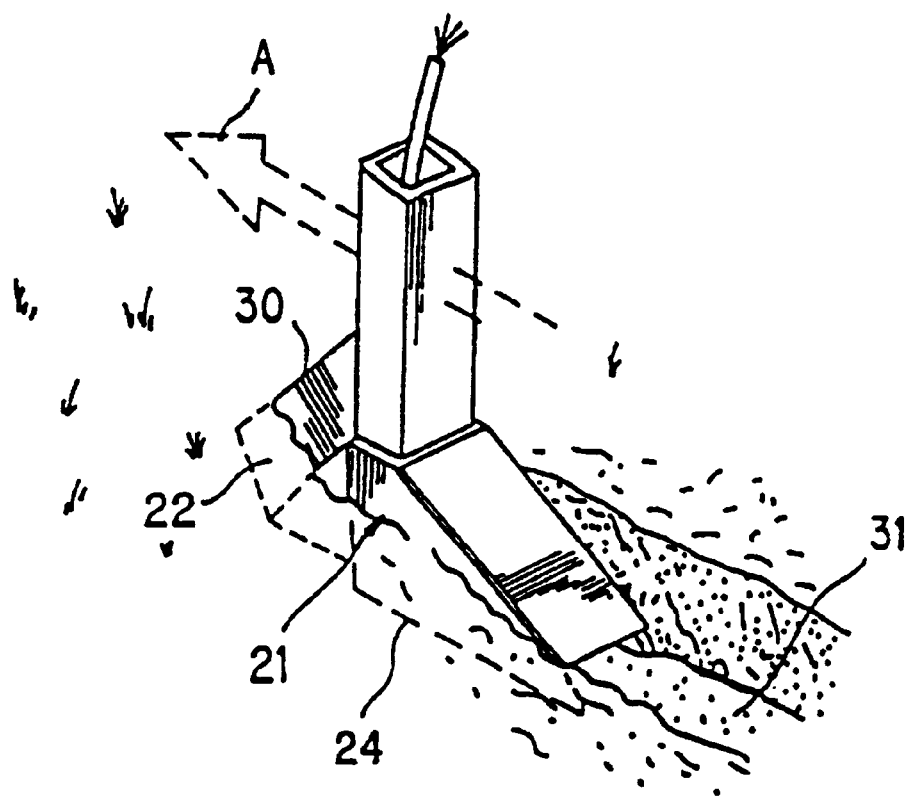
FIG. 21 illustrates how the soil characteristics are surveyed using the device to survey optical characteristics shown in FIG. 19.

FIG. 17 shows the reflectance spectrum for visible light obtained in Step 128. Wavelength is expressed on the X-axis, reflectance on the Y-axis and distance in the direction of travel on the Z-axis.

Figure 15:
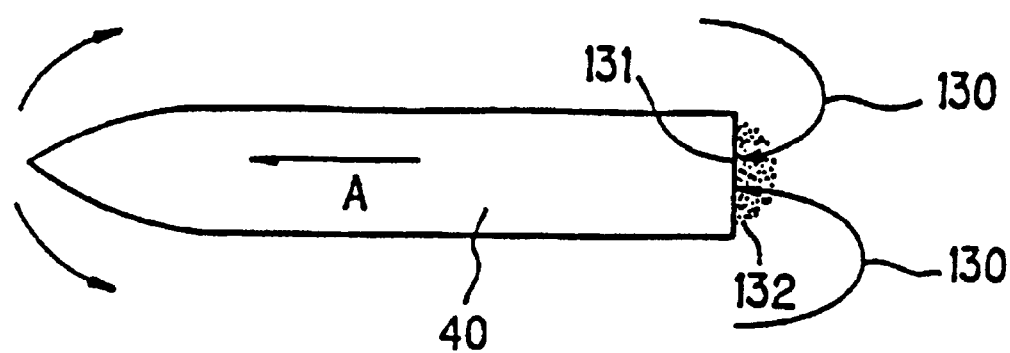
FIG. 15 illustrates what would happen if there were no opening in the rear of the device.

In this embodiment, as is shown in FIG. 5, there is an opening 64 in the lower portion of the side of sensing unit 49 which is opposite direction of progress A. As can be seen in FIG. 15, when device 40 travels through the soil in direction A, resistance will be generated in the surrounding soil in the directions indicated by arrows.

At the rear of the device, resistance will act on device 40 in the direction indicated by arrows 130. If no opening were provided, particles of soil 132 would adhere to rear wall 131. The soil 132 on rear wall 131 would enter sensing chamber 66 from below, and chamber 66 would soon fill up with soil from the surrounding area.

Figure 16:
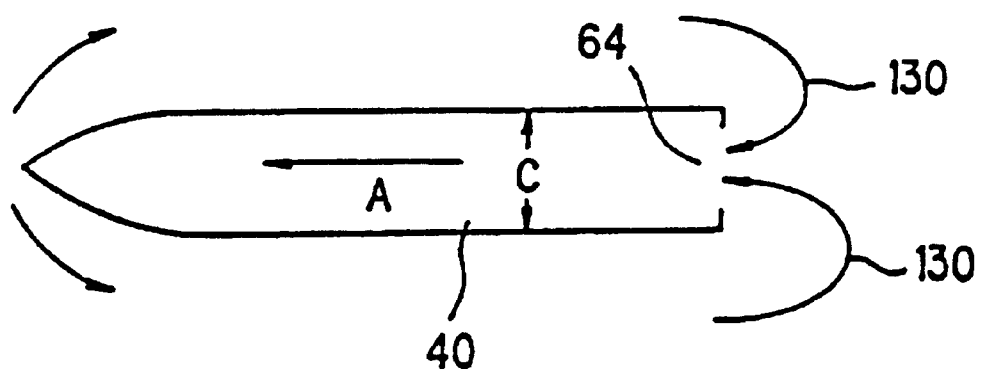
FIG. 16 illustrates how the opening in the lower portion of the rear wall of the device functions.

In this embodiment, then, as can be seen in FIG. 16, an opening 64 is provided on the lower rear portion of sensing unit 49 in device 40. Any soil which may enter sensing chamber 66 can escape through opening 64 as the device moves forward. This design prevents sensing chamber 66 from filling up with soil.

In our tests we found that no soil entered the chamber from the rear if the diameter C of device 40 was less than 3 cm. However, since the diameter of the embodiment is approximately 6 cm, it requires such an opening 64.

As was discussed earlier, in this embodiment penetration unit 55 on the front end of soil excavation unit 48 is roughly conical and has a round cross section, as does penetration unit 56, which is connected to unit 55. Thus soil excavation unit 48 creates a round tunnel as it moves through the soil. Its round cross section minimizes the resistance it experiences from the surrounding soil, allowing it to drive smoothly through the ground. This smooth passage insures that the device will not fail to survey any of the characteristics of the soil it is surveying.

As was discussed earlier, the tunnel excavated by penetration unit 55 is cylindrical. The bottom of this cylinder (i.e., its deepest portion) is rounded rather than flat. This is why a smoothing panel 60 is provided on the bottom of penetration unit 61, the segment in front of sensing unit 49. This panel flattens the heretofore curved portion on the floor of the tunnel. Since sensing unit 49 can use this flat survey surface 65 as its object of survey, it can produce a more accurate survey.

Shank 58, the part on the front end of the device which turns up the earth, is set at a slight angle opposite direction of movement A. It is shaped so as to minimize the resistance which the device experiences from the surrounding soil as it moves forward. Along the direction of movement, its cross section is long and narrow. Its tip 58a is pointed, with the point describing an acute angle of, for example, 30°. This enables the device to move through the earth while experiencing only minimal resistance and to survey soil characteristics at a considerable depth.

Sensing unit 49 is under the ground, and a vertical section of the space hollowed out by shank 58 surveys less than 3 cm. Such a small space will easily be refilled by the pressure exerted by the surrounding soil, thus effectively preventing stray light from above the ground from entering the survey chamber and insuring that the optical characteristics of the soil will be surveyed accurately.

The depth at which the soil characteristics are surveyed can be changed easily by moving the wheels (not pictured) oh either side of frame 42 up or down.

At the start of the survey, reflector panel 80 is attached below sensing unit 49 at the level where the survey is made (i.e., the level of soil survey surface 65). Using this plate, the reflectance under illumination (R) and the reflectance in the state of darkness (D) are recorded. Subsequent surveys of reflectance below ground are based on these recorded values. This insures that surveys will not be affected by the surrounding environment and so guarantees their accuracy.

An opening 64 is provided on the lower rear portion of sensing unit 49 in device 40. Any soil which may enter sensing chamber 66 will escape through opening 64 as the device moves forward. This design prevents sensing chamber 66 from filling up with soil.

When shank 58 cuts open the soil, the surrounding earth is heaped up and a long, narrow furrow is created. However, a mechanism to refill the furrow is provided so that stray light will be prevented from entering the survey chamber. This mechanism prevents the survey from being affected by stray light.

In addition to the reflectance spectrum of the soil, output data include the monitor image captured by CCD camera 68 and the temperature of the soil survey surface as surveyed by infrared emission thermometer (infrared thermocouple) 71. This allows us to correct changes in the reflectance spectrum associated with temperature changes, thus contributing to a precision field management system whose accuracy is not affected by the weather.

As has been explained in the preceding discussion, the optical soil survey device to survey the optical characteristics of a given soil, the soil survey device to survey the soil, the soil survey system and the mobile vehicle to survey the soil according to this invention achieve the following effects. In addition, we provide definitions of terms used herein to make a better understanding of the invention. It is not our intention, however, to limit the scope of the invention by these definitions.

The optical soil survey device to survey the optical characteristics of a given soil creates a survey chamber at a selected depth under the ground and surveys the spectrum of light reflected off the soil in that space continuously and in real time. This device comprises a casing which encloses at least the upper survey surface of the aforesaid space and a shank connected to the aforesaid casing which is narrower than the casing and which cuts open the soil. This device thus allows us to survey the composition of the soil, which is the most crucial ingredient in the growing of crops, at a selected depth. Because the survey chamber which it creates is below the surface of the ground, this device eliminates any effect which stray light from the exterior might have had on the survey. It allows us to survey the optical characteristics of the soil accurately in real time.

The phrase "survey chamber" refers to the chamber which is necessary to survey the soil characteristics of a surface (the "survey surface") at a given depth. If the sensor is an optical survey device, any object in the survey chamber which obstructs the light between the survey surface and the sensor will prevent surveying. It is thus necessary to create a survey chamber from which any objects that can obstruct the light between the surface and the sensor (dirt, rocks, and so on) have been removed. Since the aforesaid objects which obstruct light will not, for the most part, obstruct microwave radiation, they need not be removed from the chamber if the sensor is a device which surveys the microwave reflection and absorption characteristics of the survey surface. In this case the survey chamber will be a subterranean chamber in which a microwave transmitter and receiver are arranged in specified locations facing the survey surface.

The "casing" creates a survey chamber under the soil as it advances. It houses the sensor and forms the survey surface. The term "shank" refers to the component which keeps the casing in the soil and cuts open the soil. Shank 58 in the preferred embodiment is, of course, such a shank. If a component to cut open the soil is provided separately on the front survey surface of a stanchion to keep the casing in the soil, the entirety of the stanchion and the component to cut open the soil correspond to the shank.

The "optical survey device to survey optical characteristics" optically surveys the soil which is the object of survey and surveys its characteristics. The term includes, for example, devices which capture the image of the soil with a camera and survey its characteristics using the image data obtained or which survey soil characteristics using reflected waves.

The following definitions apply to the foregoing description of preferred embodiments of the invention. The term "survey chamber" refers to the space above the survey surface of the soil inside sensing chamber 66. The preferred embodiment has a "casing" 66a and a "shank" 58. The phrase "optical survey device to survey optical characteristics" refers to device 40 to survey the optical characteristics of the soil.

The device to survey the optical characteristics of a given soil comprises a casing which encloses at least the upper surface of the aforesaid space; a shank connected to the aforesaid casing, which is narrower than the casing and which cuts open the soil; a means to detect position data, which detects data associated with the position of the soil which is to be the subject of the aforesaid survey; and a means to survey the spectrum of the light reflected off the aforesaid soil. This device obtains in tandem the position data and the spectrum of the reflected light, thus enabling accurate precision field management.

The phrase "position data" refers to two-dimensional position data on the horizontal surface of the soil at the survey. The position detecting means to detect the position data may be an integrated survey system which combines position or bearing sensors employing the DGPS or GPS satellites with distance sensors.

The phrase "spectrum of light" refers to the intensity of the spectra of the reflected light when light is projected on the soil which is the object of survey. The intensity of the light reflected of the soil will vary with its granularity, moisture content, chemical properties, color and other characteristics. We can, then, discover the characteristics of the soil by projecting light on it and surveying the intensity spectrum of the reflected light.

Position sensor 86 is an example of a "position detecting means to detect position." The position detection means acquires data from DGPS satellite 14 and uses them to calculate position data. The phrase "spectrum of light surveying means to survey the spectra of the reflected light" refers to optical fiber 69, which gathers visible reflected light; optical fiber 70, which gathers near-infrared reflected light; spectrometer 43; and data processing unit 87.

The device to survey the optical characteristics of a given soil creates a survey chamber at a selected depth under the ground and surveys the spectrum of light reflected off the soil in that space continuously and in real time. It comprises a casing which encloses at least the upper surface of the aforesaid space; a shank connected to the aforesaid casing, which is narrower than the casing and which cuts open the soil; a means to detect position data, which detects data associated with the position of the soil which is to be the subject of the aforesaid survey; a means to detect data associated with the depth of the soil which is to be the subject of the aforesaid survey; and a means to survey the spectrum of the light reflected off the aforesaid soil. This device obtains in tandem the data associated with position and depth and the spectrum of the reflected light, thus enabling accurate precision field management.

The phrase "depth" refers to the depth of the survey surface whose characteristics are to be surveyed with respect to the surface of the ground. Wheel 45 is an example of a "depth detecting means to detect depth data." To be more precise, this comprises a rotary encoder (not pictured) which is mounted on the component by which support arm 44 is connected to the main part of the device. Arm 44 connects shank 58 to wheel 45. Wheel 45 is in contact with the ground surface; by rotating, it determines the height of excavation. Thus the rotational angle of arm 44 with respect to shank 58 varies with the depth of shank 58. The rotary encoder mounted on wheel 45 surveys the angle of rotation of arm 44, and the depth of the soil survey surface under survey is calculated based on the result of that survey.

The device to survey the optical characteristics of a given soil creates a survey chamber at a selected depth under the ground and surveys the spectrum of light reflected of the soil in that space continuously and in real time. It comprises a casing which encloses at least the upper surface of the aforesaid space; a shank connected to the aforesaid casing, which is narrower than the casing and which cuts open the soil; a means to detect position data, which detects data associated with the position of the soil which is to be the subject of the aforesaid survey; a means to survey the spectrum of the light reflected off the aforesaid soil; and a means to capture an image of the aforesaid soil. This device obtains as a group the data associated with the position of the soil, the spectrum of the reflected light and the image data. Because it can obtain image data, this device allows even more accurate precision field management.

The phrase "image" refers to the two-dimensional image representing the soil which is under survey. The CCD camera 68 is an "image capturing means to capture an image," which captures a colored image of soil survey surface 65, the object of survey.

The device to survey the optical characteristics of a given soil creates a survey chamber at a selected depth under the ground and surveys the spectrum of light reflected off the soil in that space continuously and in real time. It comprises a casing which encloses at least the upper surface of the aforesaid space; a shank connected to the aforesaid casing, which is narrower than the casing and which cuts open the soil; a means to detect position data, which detects data associated with the position of the soil which is to be the subject of the aforesaid survey; a means to detect data associated with the depth of the soil which is to be the subject of the aforesaid survey; a means to survey the spectrum of the light reflected off the aforesaid soil; and a means to capture an image of the aforesaid soil. This device obtains as a group data associated with the position of the soil, data associated with its depth, the spectrum of the reflected light and image data. Because it can obtain image data along with both position and depth data, this device allows even more accurate precision field management.

The device to survey the optical characteristics of a given soil creates a survey chamber at a selected depth under the ground and surveys the spectrum of light reflected off the soil in that space continuously and in real time. It comprises a casing which encloses at least the upper surface of the aforesaid space; a shank connected to the aforesaid casing, which is narrower than the casing and which cuts open the soil; a means to detect position data, which detects data associated with the position of the soil which is to be the subject of the aforesaid survey; a means to sense the characteristics of the aforesaid soil; a means to split the light which is to be collected by the aforesaid sensing means; and a means to survey the optical characteristics of the soil based on the spectral data produced by the aforesaid means to split the light. Because this device effectively prevents daylight from entering the survey chamber, the data it obtains are always accurate. And because the spectral analysis and hence the survey of the soil characteristics is based on these accurate data, the device guarantees an accurate survey of the optical characteristics of the soil.

The phrase "optical splitting" refers to extracting a desired reflected wave of a specific wavelength. A given soil will, according to its characteristics, evince a unique intensity of reflection for each specific wavelength of the reflected wave. We selectively extract a reflected wave of a specific wavelength and find its intensity of reflection. Spectrometer 43 is a "light splitting means to split light."

The aforesaid means to sense the characteristics of the soil comprises a means to project light having a wavelength in the visible and near-infrared region; a means to receive the light projected by the aforesaid projection device which has a wavelength in the visible region; a means to receive the light projected by the aforesaid projection device which has a wavelength in the near-infrared region; and a means to capture an image of the aforesaid soil. It is thus able to base its optical survey of the soil characteristics on a combination of the image data with whichever component of the reflected light is more suitable. This guarantees an accurate survey of the optical characteristics of the soil.

The aforesaid means to split the light comprises a means to split the light received by the aforesaid visible light photodetector, which has a wavelength in the visible region, and a means to split the light received by the aforesaid near-infrared photodetector, which has a wavelength in the near-infrared region. Thus the device can split both visible and near-infrared light on multiple channels at high speed, surveying the optical characteristics of the soil with great accuracy.

The device to survey the optical characteristics of a given soil has a means to receive the image data captured by the aforesaid imaging device and a means to calculate the reliability of the image data it receives from the aforesaid imaging device. If the reliability calculated by the aforesaid calculation device is low, the aforesaid means to survey the optical characteristics of a given soil does not do so. By eliminating needless survey, this device improves the efficiency of its accurate survey of soil characteristics.

"Reliability" refers to how accurately the output signal from the sensor which surveys the soil characteristics represents those characteristics. To give one example, if there are scattered rocks on the survey surface of the soil, the sensor may survey a rock instead of the soil. In this case, its output signal will have low reliability when interpreted as representing the characteristics of the soil. Reliability may be expressed as "high" or "low", or a numerical value may be used.

The reliability is the average value obtained by the processing in Step 106 of FIG. 13.

The device to survey the optical characteristics of a given soil has a means to receive the image data captured by the aforesaid imaging device and a means to calculate, based on the data received by the aforesaid means to receive image data, the reliability of the aforesaid data associated with spectral analysis. Because the aforesaid means to survey the optical characteristics of the soil stores the reliability calculated by the aforesaid calculation device, the device can eliminate needless survey and thus improve its accuracy and efficiency.

The device to survey the optical characteristics of a given soil has a means to detect the temperature of the aforesaid soil. Knowing the temperature when surveying the optical characteristics of the soil improves the accuracy of the survey.

The device to survey the optical characteristics of a given soil creates a survey chamber at a selected depth below the ground and there surveys the optical characteristics of the soil. It comprises a soil excavation unit, which excavates the soil parallel to the surface of the ground at a selected depth below the ground; a casing, which is connected to the aforesaid soil excavation unit and encloses at least the upper surface of the aforesaid survey chamber; a sensing unit, which senses the characteristics of the soil inside the aforesaid casing; a shank connected to the aforesaid casing but with a diameter which is less than that of the casing, which cuts open the soil; and two guide panels, which guide the soil piled up on the survey surface by the action of the aforesaid shank back toward the shaft created by the shank. This design allows the soil composition to be surveyed below the ground in a mobile survey chamber.

The phrase "soil excavation unit" refers to the device which advances below the surface of the soil and creates a space as it proceeds in order to provide a survey chamber. The device with an excavation tool on its front end is the soil excavation unit.

The "guide panels" guide the soil which is heaped up by the excavation back into the furrow. When the shank cuts open the soil, the excavated soil is piled on either side, and a furrow is created in the direction it is moving. This furrow can admit stray light which will cause the soil characteristics to be surveyed inaccurately. The guide panels fill this furrow by guiding the excavated soil back into it.

The preferred embodiment has a "soil excavation unit" 48 and "guide panels" such as curved plows 143 and refilling mechanism 150.

The device to survey the optical characteristics of a given soil has a penetration unit on the front of the aforesaid soil excavation unit which creates a cylindrical tunnel, and a smoothing panel which is mounted at the front of the aforesaid sensing unit to fill in the bottom of the aforesaid cylindrical tunnel and so create a flat survey surface at which to survey the characteristics of the soil. The soil excavation unit can thus excavate a cylindrical hole as it moves through the soil. This minimizes the resistance it experiences from the surrounding earth, allowing it to proceed smoothly, and insuring that no soil characteristics will be missed in the survey. The smoothing panel creates a flat survey surface on the floor of the formerly cylindrical tunnel. This permits a more accurate survey to be performed.

The phrase "penetration unit" refers to the tool on the front of the excavation unit which excavates the soil. The term "cylindrical tunnel" refers to a curve with a smoothly tapering contour such as a portion of a circle or an ellipse. The term "smoothing panel" refers to the tool which flattens the floor of the tunnel created by the penetration unit. If a panel is provided to create a flat soil survey surface on the floor of the tunnel, it may be either flat or curved. The preferred embodiment has a "penetration unit" 55 and 56 and a "smoothing panel" 60. The term "survey surface" refers to the surface of the soil inside the casing. This is the surface which will be surveyed by the sensor installed on the ceiling of the chamber in the casing. If this surface is not flat, the survey will be inaccurate.

The device to survey the optical characteristics of a given soil has an opening in the rear wall of the aforesaid sensing unit so that any soil which gets into the chamber can escape through the rear. This prevents the sensing chamber from filling up with soil.

The term "opening" refers to the hole 64 in the rear of the casing through which the soil can escape. According to this invention, the device advances below the surface of the soil. As it proceeds, the soil cut open by the shank begins to adhere to the rear wall of the casing. As this soil falls into the casing, the casing begins to fill up. To prevent this, this invention left the rear wall of the chamber partly open, thus creating a way for the soil in the casing to escape.

The aforesaid shank is placed on top of the aforesaid soil excavation unit and angled slightly away from the direction in which the device moves. It projects upward toward the surface of the ground. Its tip, which breaks the soil, forms an acute angle. This design allows the device to experience minimal resistance as it travels through the earth and enables it to survey soil characteristics at considerable depth.

The device to survey a given soil surveys the soil as it moves parallel to the surface of the ground. It comprises a sensor to survey the soil; a casing, which encloses at least the upper surface and two sides of the survey chamber in which the aforesaid sensor is to survey the soil; a soil excavation unit, which is on the front of the aforesaid casing and which excavates the soil as the device moves through it; a shank, which is connected to the top of the aforesaid casing, which protects that casing, and which has a V-shaped portion on at least a part of its surface which is in contact with the earth to cut open the soil as the device moves along horizontally. This design allows the device to travel through the soil while preventing stray light from compromising the survey. Because the shank has a V-shaped portion to cut through the soil, the survey device experiences minimal resistance as it progresses.

The term "sensor" refers not only to optical, and electrical, but also chemical, physical, and any other types of sensors which are available to sense the characteristics of soil.

The aforesaid sensor is supported within the aforesaid casing facing downward toward the subject of detection. In the rear of the casing and below the sensor an opening is provided. This opening in the rear of the aforesaid casing is large enough to prevent the chamber from filling up with particles of the soil turned up by the aforesaid soil excavation unit. The aforesaid sensor is mounted far enough from the aforesaid opening so that any soil which may enter through the aforesaid rear opening will not end up in the survey area defined by the aforesaid sensor. This design prevents the chamber from filling up when soil from the walls of the shaft collapses into the opening in the rear of the casing. If this soil could not escape, it would obstruct the opening, and the soil moving through the chamber would adhere to it. The survey area of the sensor would be covered with soil which was not supposed to be surveyed.

A panel to smooth the survey surface of the soil cut open by the front of the aforesaid casing is supported by the casing in such a way that it is angled downward toward the surface where it comes in contact with the earth. This panel is mounted in front of the survey region overseen by the sensor in the aforesaid portion with an opening. This will prevent extraneous soil from getting into the survey region. By leveling the soil which is the subject of survey, the panel insures that the conditions under which the soil's characteristics are surveyed will remain stable. This stability enhances the reliability of the data obtained by the survey.

The aforesaid soil excavation unit has a round cross section and it digs a cylindrical tunnel. The aforesaid smoothing panel flattens a portion of that tunnel so that its floor is level. A tunnel with a round cross section has a smaller circumference than a square tunnel. This design minimizes the resistance of the earth which acts on the soil excavation unit as it travels through the ground.

The soil survey device surveys a given soil. It comprises an illumination device to survey the soil; a device to capture a two-dimensional image, which uses the illumination of the aforesaid device to survey the soil; a sensor which surveys the portion of the soil in the region imaged by the aforesaid imaging device and outputs a signal corresponding to the composition of the surveyed soil; a means to generate a feature count, which processes the image of the soil captured by the aforesaid imaging device and generates a feature count expressing the unevenness of the soil surface; and a means to calculate reliability, which calculates and outputs the reliability of the signal output by the aforesaid sensor based on the feature count generated by the aforesaid generating means. If there are rocks scattered over the survey surface of the soil and the sensor surveys a rock instead of the soil, its output signal will have low reliability as representing the characteristics of the soil. The reliability, which is the degree to which the output signal from the sensor represents the characteristics of the soil, will vary depending on how uneven the soil survey surface is. In general, an extremely uneven survey surface will result in low reliability. Since the state of the survey surface, i.e., whether it contains extraneous objects or is uneven, can be discerned from the image obtained by the imaging device, we can use this image to generate the reliability of the output signal from the sensor which surveys the soil. This allows us to use post-processing such as eliminating signals whose reliability is below a reference value. The result is a more accurate treatment of soil data.

The phrase "feature count expressing the unevenness" refers to the unevenness of the soil surface. If there are clods of large diameter on the surface, it will be uneven. If the soil surface is uneven, it will be difficult to obtain a signal representing the characteristics of the soil.

The "feature count expressing the unevenness" is surveyed by the processing in FIG. 13, and in particular by the processing in Steps 100 through 106.

The soil survey device surveys a given soil. It comprises an illumination device to survey the soil; a device to capture a two-dimensional image, which uses the illumination of the aforesaid device to survey the soil; a means to generate a feature count, which processes the image of the soil survey surface captured by the aforesaid device and generates a feature count which expresses how uneven the soil is; a means to generate multichannel data, which processes the image captured by the aforesaid device and obtains data associated with the optical characteristics of each of a number of wavelength regions of the light reflected off the soil; and a means to calculate reliability, which calculates and outputs the reliability of the data output by the aforesaid means to generate multichannel data based on the feature count generated by the aforesaid generating means. With a single image from a color camera, then, this device can acquire data representing the characteristics of the soil along with their reliability. This allows us to use post-processing such as eliminating signals whose reliability is below a reference value. The result is a more accurate treatment of soil data which is achieved with a simple device.

The soil survey device surveys a given soil. It comprises an illumination device to illuminate the soil surface; a first image capturing device to capture a two-dimensional image, which survey the soil surface illuminated by said illumination device; a sensor which surveys the portion of the soil surface imaged by said first image capturing device and outputs a signal corresponding to the composition of the surveyed soil; and a soil structure detecting means to detect the structure of the soil surface based on the two-dimensional image of the soil surface captured by said first image capturing device. This design allows us to record the data for the soil structure and the soil composition, and it allows us to manage the field with a simple device.

The term "composition" refers to data concerning the makeup of the soil, including its type, chemical nature, viscosity and granularity. In the preferred embodiment, the "composition" are the data obtained by the processing in Step 124 of FIG. 14.

The soil survey device to survey the soil does so while moving through the ground horizontally. It comprises an illumination device to illuminate the soil surface; a first image capturing device to capture a two-dimensional image, which survey the soil surface illuminated by said illumination device; a sensor which surveys the portion of the soil surface imaged by said first image capturing device and outputs a signal corresponding to the composition of the surveyed soil; a first feature counting means to generate a feature count, which processes the image of the soil captured by said first image capturing device and generates a feature count expressing the unevenness of the soil surface; a first reliability calculating means to calculate reliability, which calculates and outputs the reliability of the signal output by said sensor based on the feature count generated by said first feature counting means; a casing which encloses at least the upper surface and two sides of a survey chamber in which said sensor is to survey the soil; a soil excavation unit which is provided on the front of said casing and which excavates the underground soil as said soil survey device moves forward; a shank which is connected to the top of said casing and protects said casing, and which has a V-shaped portion on at least a tip in contact with the earth to cut open the soil as said device moves along horizontally, said shank being further characterized that the width of said shank is narrower than said casing; and a pair of guide panels which guide the soil piled up on the soil surface by the action of said shank back toward the shaft created by said shank. This design allows us to survey the soil continuously and gather data associated with the composition of the soil and its various components as the device is moving. This design allows us to survey the soil continuously abased on the reliable data while moving.

The soil survey device to survey the soil does so while moving through the ground horizontally. It comprises an illumination device to survey the soil; a device to capture a two-dimensional image, which uses the illumination of the aforesaid device to survey the soil; a sensor, which surveys the portion of the soil imaged by the aforesaid imaging device and outputs a signal corresponding to the components of the surveyed soil; a means to detect the composition of the soil, which processes the image of the soil survey surface captured by the aforesaid imaging device and detects data associated with the composition of the soil survey surface; a casing, which encloses at least the top and two sides of the survey space, the space in which the aforesaid sensor and imaging device survey the soil; a soil excavation unit, which is on the front of the aforesaid casing, and which excavates the soil as the device moves through the earth; a shank, which is connected to the top of the aforesaid casing, which supports the casing, and which has a V-shaped portion on at least a part of its surface which is in contact with the earth to cut open the soil as the device moves along horizontally; and two guide panels, which guide the soil piled up on the surface by the action of the aforesaid shank back toward the shaft created by the shank. This design allows us to survey the soil continuously and gather data associated with the composition of the soil and its various components as the device is moving.

The system to survey a given soil comprises any one of the soil survey devices previously described; a data acquisition device, which acquires data related to the current position of the soil survey device; and a data recording device, which records the data output by the aforesaid soil survey device and those output by the aforesaid device to acquire position data as a set. With these data, the system is able to compose a map of the soil.

The system to survey a given soil comprises any one of the soil survey devices previously described; a data acquisition device, which acquires data related to the current position of the soil survey device; and a data transmission device, which transmits in tandem the data output by the aforesaid soil survey device and those output by the aforesaid device to acquire position data. Thus this system can transmit data which the receiving device can use to compose a map of the soil.

The mobile survey vehicle comprises either of the soil survey systems previously described and a vehicle which carries the aforesaid survey system over the surface of the ground. This system can thus map the soil in real time as the vehicle travels over the field or plot.

The mobile survey vehicle comprises any one of the soil survey devices previously described; a data acquisition device, which acquires data related to the current position of the soil survey device; a means to survey depth, which surveys the depth of the soil survey surface surveyed by the aforesaid soil survey device; a data recording device, which records as a single set the data output by the aforesaid soil survey device, the data output by the aforesaid device to acquire position data and those output by the aforesaid survey device; and a vehicle which carries the aforesaid soil survey device, the device to acquire position data and the aforesaid means to survey depth over the surface of the ground. This system can thus create a map of the soil including depth data as the vehicle is moving.

The mobile survey vehicle comprises the mobile surveillance vehicle previously described. Two arms which are capable of rotation are mounted to the sides of the aforesaid shank, which is itself mounted to the aforesaid vehicle in such a way that they are free to rotate. Freewheels on their forward extremities are in contact with the earth. Based on the result of surveying the angle of the aforesaid arms, the aforesaid means to survey depth calculates the depth of the soil survey surface which is the subject of survey. This design offers a simple means for data concerning the depth of the soil survey surface to be acquired and allows a soil map to be produced which includes depth data.

The present invention should not be limited to the preferred embodiments described and shown herein. Instead, the invention should be defined by the following claims.

What is claimed is:

1. An optical soil survey device for precision field management to survey the optical characteristics of a given soil by creating a survey chamber at a selected depth under the ground and surveying the spectrum of light reflected off the soil in the chamber continuously and in real time, said optical soil survey device comprising:
   a casing which encloses at least an upper survey surface of the chamber;
   a shank connected to said casing which is narrower than said casing and which cuts open the soil and declined slightly backwardly;
   a soil excavation unit having a first penetration unit which is a conical shaped piece with a tapered front end, and a second penetration unit with a gradual increase in diameter which extends away from said first penetration unit, so as to form a space between the ground and said second penetration unit, said soil excavation unit being mounted in front of said casing and held in horizontal direction; and
   a position detecting means to detect a position of the soil which is to be the subject of the survey; and
   a spectrum of light surveying means to survey the spectrum of light reflected off the soil at the position detected by said position detecting means, thereby producing survey data of the spectrum of light corresponding to each position data.

2. An optical soil survey device according to claim 1, further comprising a depth detecting means to detect the depth of the soil, thereby producing survey data of each spectrum of light corresponding to the position and the depth.

3. An optical soil survey device according to claim 1, further comprising an image capturing means to capture an image of the soil, thereby producing survey data of each spectrum of light and each image of the soil corresponding to the position.

4. An optical soil survey device according to claim 1, further comprising:
   a depth detecting means to detect the depth of the soil, and
   an image capturing means to capture an image of the soil, thereby producing survey data of each spectrum of light and each image of the soil corresponding to the position and the depth.

5. An optical soil survey device according to claim 1, further comprising:
   a position detecting means to detect a position of the soil which is to be the subject of the survey;
   a sensing means to sense the characteristics of the soil;
   a light splitting means to split the light, which is to be collected by said sensing means; and
   an optical characteristics survey means to survey the optical characteristics of the soil based on the spectral data produced by said light splitting means.

6. An optical soil survey device according to claim 5, wherein said sensing means comprises:
   a light projecting means to project light having a wavelength in the visible and near-infrared region;
   a first light receiving means to receive the light projected by said light projecting means which has a wavelength in the visible region;
   a second light receiving means to receive the light projected by said light projecting means which has a wavelength in the near-infrared region; and
   an image capturing means to capture an image of the soil.

7. An optical soil survey device according to claim 6, wherein said light splitting means comprises:
   a first light splitting means to split the light received by said first light receiving means, which has a wavelength in the visible region; and
   a second light splitting means to split the light received by said second light receiving means, which has a wavelength in the near-infrared region.

8. An optical soil survey device according to claim 6, further comprising:
   an image receiving means to receive the image data captured by said image capturing means; and
   a reliability calculating means to calculate the reliability of the received split light by the image data received by said image receiving means, thereby canceling the survey of the soil if the reliability calculated by said reliability calculating means is low.

9. An optical soil survey device according to claim 8, wherein said reliability calculating means calculate said reliability by shooting a slit beam to the surface of the soil surface.

10. An optical soil survey device according to claim 6, further comprising:
   an image receiving means to receive the image data captured by said image capturing means; and a reliability calculating means to calculate the reliability of the received split light by the image data received by said image receiving means, thereby storing the reliability calculated by the calculation device.

11. An optical soil survey device according to claim 10, wherein said reliability calculating means calculate said reliability by shooting a slit beam to the surface of the soil surface.

12. An optical soil survey device according to claim 6, further comprising a temperature detecting means to detect the temperature of the soil.

13. An optical soil survey device for precision field management to survey the optical characteristics of a given soil creating a survey chamber at a selected depth under the ground and surveying the spectrum of light reflected off the soil in the chamber continuously, said optical soil survey device comprising:

a soil excavation unit which excavates the soil parallel to the surface of the ground at a selected depth below the ground, said soil excavation unit having a first penetration unit which is a conical shaped piece with a tapered front end, and a second penetration unit with a gradual increase in diameter which extends away from said first penetration unit, so as to form a space between the ground and said second penetration unit, said soil excavation unit being held in horizontal direction;

a casing which is connected to said soil excavation unit and encloses at least the upper surface of the survey chamber;

a sensing unit which senses the characteristics of the soil inside said casing;

a shank connected to said casing but with a diameter which is less than that of said casing, and declined slightly backwardly, which cuts open the soil; and a pair of guide panels which guide the soil piled up on the survey surface by the action of said shank back toward the shaft created by said shank.

14. An optical soil survey device according to claim 13, further comprising:

a penetration unit on the front of said soil excavation unit, which creates a cylindrical tunnel; and a smoothing pan el which is mounted at the front of said sensing unit to create a flat survey surface at the bottom of the cylindrical tunnel, and said sensing unit thereby surveying the characteristics of the soil.

15. An optical soil survey device according to claim 13, further comprising an opening in the rear side of said sensing unit so that any soil which gets into the survey chamber can escape through the rear.

16. An optical soil survey device according to claim 13, wherein said shank is placed on top of said soil excavation unit and angled slightly away from the direction in which said device moves.

17. A soil survey device used for precision field management to survey a given underground soil surface while moving parallel to the surface of the ground, comprising:

a sensor to survey the soil;

a casing which encloses at least the upper surface and two sides of a survey chamber in which said sensor is to survey the soil;

a soil excavation unit which is provided on the front of said casing and which excavates the underground soil as said soil survey device moves forward, said soil excavation unit having a first penetration unit which is a conical shaped piece with a tapered front end, and a second penetration unit with a gradual increase in diameter which extends away from said first penetration unit so as to form a space between the ground and said second penetration unit, said soil excavation unit being held in horizontal direction; and a shank which is connected to the top of said casing and protects said casing and declined slightly backwardly, and which has a V-shaped portion on at least a tip in contact with the earth to cut open the soil as said device moves along horizontally, and wherein said shank is narrower than said casing.

18. A soil survey device according to claim 17, wherein said sensor is supported within said casing facing downward toward the subject of sensing, said casing is provided with a continuous opening from the bottom to the rear of said casing, said rear opening of said casing is small enough to prevent the survey chamber from filling up with particles of the soil turned up by said soil excavation unit, and said sensor is mounted far enough from the rear opening so that any soil which may enter through the rear opening will not end up in the surveying area defined by said sensor.

19. A soil survey device according to claim 18, further comprising a smoothing panel to smooth the survey surface of the soil cut open by the front of said casing, said smoothing panel being supported by said casing in such a way that said smoothing panel is angled downward toward the survey surface.

20. A soil survey device according to claim 18, wherein said soil excavation unit has a round cross section and digs a cylindrical tunnel, said smoothing panel flattens a portion of the tunnel so that the floor of the tunnel is level.

21. A soil survey device used for precision field management to survey a given underground soil surface while moving parallel to the surface of the ground, comprising:

an illumination device to illuminate the soil surface;

a first image capturing device to capture a two-dimensional image, which surveys the soil surface illuminated by said illumination device;

a sensor which surveys the portion of the soil surface imaged by said first image capturing device and outputs a signal corresponding to the composition of the surveyed soil;

a first feature counting means to generate a feature count, which processes the image of the soil captured by said first image capturing device and generates a feature count expressing the unevenness of the soil surface;

a first reliability calculating means to calculate reliability, which calculates and outputs the reliability of the signal output by said sensor based on the feature count generated by said first feature counting means;

a casing which encloses at least the upper surface and two sides of a survey chamber in which said sensor is to survey the soil;

a soil excavation unit which is provided on the front of said casing and which excavates the underground soil as said soil survey device moves forward, said soil excavation unit having a first penetration unit which is a conical shaped piece with a tapered front end, and a second penetration unit with a gradual increase in diameter which extends away from said first penetration unit so as to form a space between the ground and said second penetration unit, said soil excavation unit being held in horizontal direction;

a shank which is connected to the top of said casing and protects said casing and declined slightly backwardly, and which has a V-shaped portion on at least a tip in contact with the earth to cut open the soil as said device moves along horizontally, the width of said shank being narrower than said casing; and a pair of guide panels which guide the soil piled up on the soil surface by the action of said shank back toward the furrow created by said shank.

22. An optical soil survey device according to claim 21, wherein said reliability calculating means calculate said reliability by shooting a slit beam to the surface of the soil surface.

23. A soil survey device used for precision field management to survey a given underground soil surface while moving parallel to the surface of the ground, comprising:

an illumination device to illuminate the soil surface;

a first image capturing device to capture a two-dimensional image, which surveys the soil surface illuminated by said illumination device;

a sensor which surveys the portion of the soil surface imaged by said first image capturing device and outputs a signal corresponding to the composition of the surveyed soil;

a first feature counting means to generate a feature count, which processes the image of the soil captured by said first image capturing device and generates a feature count expressing the unevenness of the soil surface;

a casing which encloses at least the upper surface and two sides of a survey chamber in which said sensor is to survey the soil;

a soil excavation unit which is provided on the front of said casing and which excavates the underground soil as said soil survey device moves forward, said soil excavation unit having a first penetration unit which is a conical shaped piece with a tapered front end, and a second penetration unit with a gradual increase in diameter which extends away from said first penetration unit so as to form a space between the ground and said second penetration unit, said soil excavation unit being held in horizontal direction; and a shank which is connected to the top of said casing and protects said casing and declined slightly backwardly, and which has a V-shaped portion on at least a tip in contact with the earth to cut open the soil as said device moves along horizontally, the width of said shank is narrower than said casing; and a pair of guide panels which guide the soil piled up on the soil surface by the action of said shank back toward the furrow created by said shank.

24. A soil survey system to survey a given underground soil surface used for precision field management, comprising:

a soil survey device used for precision field management to survey a given underground soil surface while moving parallel to the surface of the ground, said soil survey device comprising:

a sensor to survey the soil;

a casing which encloses at least the upper surface and two sides of a survey chamber in which said sensor is to survey the soil;

a soil excavation unit which is provided on the front of said casing and which excavates the underground soil as said soil survey device moves forward, said soil excavation unit having a first penetration unit which is a conical shaped piece with a tapered front end, and a second penetration unit with a gradual increase in diameter which extends away from said first penetration unit so as to form a space between the ground and said second penetration unit, said soil excavation unit being held in horizontal direction;

a shank which is connected to the top of said casing and protects said casing and declined slightly backwardly, and which has a V-shaped portion on at least a tip in contact with the earth to cut open the soil as said device moves along horizontally, said shank being narrower than said casing;

said soil survey system further comprising:

a current position data acquisition device to acquire the current position of said soil survey device; and a data recording means to record a surveying data of the output data obtained from said soil survey device and the position data obtained from said current position data acquisition device.

25. A soil survey system according to claim 24, further comprising a data transmission means to transmit said surveying data obtained from said data recording means.

26. A mobile survey vehicle to move in a field equipped with a soil survey system to survey a given underground soil surface used for precision field management, said soil survey system comprising:

a soil survey device used for precision field management to survey a given underground soil surface while moving parallel to the surface of the ground, said soil survey device comprising:

a sensor to survey the soil;

a casing which encloses at least the upper surface and two sides of a survey chamber in which said sensor is to survey the soil;

a soil excavation unit provided on the front of said casing and which excavates the underground soil as said soil survey device moves forward, said soil excavation unit having a first penetration unit which is a conical shaped piece with a tapered front end, and a second penetration unit with a gradual increase in diameter which extends away from said first penetration unit so as to form a space between the ground and said second penetration unit, said soil excavation unit being held in horizontal direction;

a shank which is connected to the top of said casing and protects said casing and declined slightly backwardly, and which has a V-shaped portion on at least a tip in contact with the earth to cut open the soil as said device moves along horizontally, said shank being further characterized that the width of said shank is narrower than said casing;

said soil survey system further comprising:

a current position data acquisition device to acquire the current position of said soil survey device; and a data recording means to record a surveying data of the output data obtained from said soil survey device and the position data obtained from said current position data acquisition device.

27. A mobile survey vehicle for use in precision field management, said mobile survey vehicle adapted to survey a given underground soil surface while moving parallel to the surface of the ground, said mobile survey vehicle comprising:

a soil survey device, comprising:

a sensor to survey the soil;

a casing which encloses at least the upper surface and two sides of a survey chamber in which said sensor is to survey the soil;

a soil excavation unit which is provided on the front of said casing and which excavates the underground soil as said soil survey device moves forward, said soil excavation unit having a first penetration unit which is a conical shaped piece with a tapered front end, and a second penetration unit with a gradual increase in diameter which extends away from said first penetration unit so as to form a space between the ground and said second penetration unit, said soil excavation unit being held in horizontal direction; and a shank which is connected to the top of said casing and protects said casing and declined slightly backwardly, and which has a V-shaped portion on at least a tip in contact with the earth to cut open the soil as said device moves along horizontally, said shank being narrower than said casing;

wherein said mobile survey vehicle further comprises:
  a current position data acquisition device to acquire the current position of said soil survey device;
  a depth surveying means to survey depth, which surveys the depth of the soil survey surface surveyed by said soil survey device; and
  a data recording means to record a surveying data of the output data obtained from said soil survey device, and the position data obtained from said current position data acquisition device and the depth data obtained from said depth surveying means.

28. A mobile survey vehicle according to claim 27, wherein said depth surveying means comprises a wheel rotatably supported by an arm which is connected to said shank, said wheel being rotated on the surface of the ground as said mobile survey vehicle moves, such that said depth data is calculated from the angle of said arm.

29. An optical soil survey device for precision field management to survey the optical characteristics of a given soil by creating a survey chamber at a selected depth under the ground and surveying the spectrum of light reflected off the soil in the chamber continuously and in real time, said optical soil survey device comprising:
  a casing which encloses at least an upper survey surface of the chamber;
  a shank connected to said casing which is narrower than said casing and which cuts open the soil and declined slightly backwardly;
  a soil excavation unit having a first penetration unit which is a conical shaped piece with a tapered front end, and a second penetration unit with a gradual increase in diameter which extends away from said first penetration unit, so as to form a space between the ground and said second penetration unit, said soil excavation unit being mounted in front of said casing and held in horizontal direction; and
  a position detecting means to detect a position of the soil which is to be the subject of the survey;
  a sensing means to sense the characteristics of the soil;
  a light splitting means to split the light, which is to be: collected by said sensing means; and
    an optical characteristics survey means to survey the optical characteristics of the soil based on the spectral data produced by said light splitting means.

* * * * *